(12) United States Patent
Wang et al.

(10) Patent No.: US 12,410,123 B2
(45) Date of Patent: Sep. 9, 2025

(54) N-[8-(2-HYDROXYBENZOYL)AMINO]POTASSIUM OCTANOATE CRYSTAL POLYMORPH, AND PREPARATION METHOD THEREFOR AND USE THEREOF

(71) Applicant: SCIWIND BIOSCIENCES CO., LTD., Hangzhou Zhejiang (CN)

(72) Inventors: Hongyang Wang, Beijing (CN); Shiyue Jiang, Beijing (CN); Yao Li, Beijing (CN); Hai Pan, Beijing (CN)

(73) Assignee: SCIWIND BIOSCIENCES CO., LTD., Hangzhou Zhejiang (CN)

( * ) Notice: Subject to any disclaimer, the term of this patent is extended or adjusted under 35 U.S.C. 154(b) by 502 days.

(21) Appl. No.: 17/999,945

(22) PCT Filed: Nov. 11, 2020

(86) PCT No.: PCT/CN2020/128050
§ 371 (c)(1),
(2) Date: Nov. 28, 2022

(87) PCT Pub. No.: WO2021/238088
PCT Pub. Date: Dec. 2, 2021

(65) Prior Publication Data
US 2023/0234916 A1    Jul. 27, 2023

(30) Foreign Application Priority Data
May 29, 2020    (WO) ................ PCT/CN2020/093306

(51) Int. Cl.
*C07C 235/60*    (2006.01)
*A61K 31/20*    (2006.01)
*A61K 38/26*    (2006.01)

(52) U.S. Cl.
CPC ............ *C07C 235/60* (2013.01); *A61K 31/20* (2013.01); *A61K 38/26* (2013.01); *C07B 2200/13* (2013.01)

(58) Field of Classification Search
CPC ...... C07C 235/60; A61K 31/20; A61K 38/26; C07B 2200/13
See application file for complete search history.

(56) References Cited

U.S. PATENT DOCUMENTS

| 5,650,386 A | 7/1997 | Leone-Bay et al. |
| 8,026,392 B2 * | 9/2011 | Dhoot ...................... A61P 3/14 562/450 |
| 8,636,996 B2 | 1/2014 | Levchik et al. |
| 2009/0143330 A1 | 6/2009 | Levchik et al. |
| 2021/0393744 A1 | 12/2021 | Xu et al. |

FOREIGN PATENT DOCUMENTS

| CN | 1953753 A | 4/2007 |
| CN | 102001962 A | 4/2011 |
| CN | 109069475 A | 12/2018 |
| CN | 111517980 A | 8/2020 |
| WO | WO 2005/107462 A2 | 11/2005 |
| WO | WO 2008/028859 A1 | 3/2008 |
| WO | WO 2012/080471 A1 | 6/2012 |
| WO | WO 2017/185038 A1 | 10/2017 |
| WO | WO 2019/201328 A1 | 10/2019 |

OTHER PUBLICATIONS

China National Intellectual Property Administration, International Search Report in International Application No. PCT/CN2020/128050 (Mar. 3, 2021).
China National Intellectual Property Administration, Written Opinion in International Application No. PCT/CN2020/128050 (Mar. 3, 2021).
International Bureau of WIPO, International Preliminary Report on Patentability in International Application No. PCT/CN2020/128050 (Nov. 17, 2022).

* cited by examiner

*Primary Examiner* — Kamal A Saeed
(74) *Attorney, Agent, or Firm* — Leydig, Voit & Mayer, Ltd.

(57) ABSTRACT

Disclosed in the present application is a crystal polymorph of potassium N-[8-(2-hydroxybenzoyl)amino]octanoate, wherein the crystal polymorph of potassium N-[8-(2-hydroxybenzoyl)amino]octanoate is crystal Form I, and the crystal Form I has at least an X-ray powder diffraction pattern with characteristic peaks represented by 2θ° of 7.83±0.2, 26.64±0.2 and 18.89±0.2. The crystal polymorph of potassium N-[8-(2-hydroxybenzoyl)amino]octanoate provided by the present application has four crystal forms, has high solubility and strong stability, can deliver drugs more effectively, increases the permeability of the delivered drugs in the gastrointestinal tract, and is beneficial to the preparation of oral preparations, such that preventive and/or therapeutic drugs can be better delivered into the body to achieve the effect of improving the bioavailability.

19 Claims, 11 Drawing Sheets

N-[8-(2-HYDROXYBENZOYL)AMINO]POTASSIUM OCTANOATE CRYSTAL POLYMORPH, AND PREPARATION METHOD THEREFOR AND USE THEREOF

CROSS-REFERENCE TO RELATED APPLICATIONS

This patent application is the U.S. national phase of International Application No. PCT/CN2020/128050, filed on Nov. 11, 2020, which claims the benefit of International Application No. PCT/CN2020/093306, filed May 29, 2020, the disclosures of which are incorporated herein by reference in their entireties for all purposes.

TECHNICAL FIELD

The present application relates to the field of chemical medicine, in particular to a crystal polymorph of potassium N-[8-(2-hydroxybenzoyl)amino]octanoate and a preparation method and use thereof.

BACKGROUND ART

Macromolecular drugs such as peptides and protein drugs are often not easily absorbed into the intestinal tract by oral administration due to their characteristics such as large molecular weight, low lipid solubility, unstable to gastric acid, and being destructible by various digestive enzymes in the gastrointestinal tract. In response to the above problems, people have tried to overcome drug absorption barriers from various aspects. In addition to some attempts in dosage forms, gastrointestinal absorption enhancers are often used to improve biofilm permeability of drugs. Although it increases the absorption of drugs, it also increases the absorption of intestinal endotoxins and lacks safety for long-term use.

A new type of macromolecular drug delivery agent N-[8-(2-hydroxybenzoyl)amino]octanoic acid (NAC for short) and a salt thereof are disclosed in U.S. Patent U.S. Pat. No. 5,650,386 (published in 1997), and its molecular formula is as shown in Formula (I). Particularly, U.S. Patent U.S. Pat. No. 8,636,996 (published in 2009) discloses the polymorphic form, amorphous form and preparation method thereof of monosodium N-[8-(2-hydroxybenzoyl)amino]octanoate (abbreviated as SNAC), and its molecular formula is as shown in Formula (11).

Formula (I)

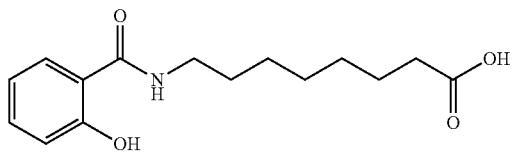

Formula (II)

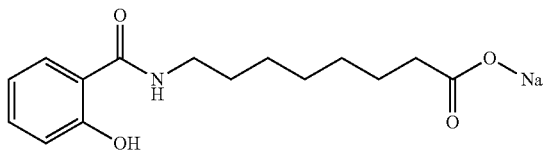

SNAC is a novel amino acid derivative delivery agent. Recent studies have shown that, it may promote the oral absorption of various protein drug solutions such as heparin and human growth hormone without the need for dosage form protection, but does not show obvious cytotoxicity. Since the bioavailability, solubility and fluidity of different salt forms of a compound will also vary, different crystal forms of the same salt form will have different crystal shape, density, hardness, color, chemical stability, melting point, hygroscopicity, suspendability and dissolution rate and other characteristics, which will directly or indirectly affect the ability of the delivered drug, resulting in differences in the bioavailability, compressibility, and stability of the delivered drug.

SUMMARY OF THE INVENTION

The object of this application is to provide a crystal polymorph of potassium N-[8-(2-hydroxybenzoyl)amino] octanoate and preparation method and use thereof, the pharmaceutical composition and use thereof.

The technical solutions of this application are as follows:

1. A crystal polymorph of potassium N-[8-(2-hydroxybenzoyl)amino]octanoate, characterized in that the crystal polymorph of potassium N-[8-(2-hydroxybenzoyl)amino] octanoate is crystal Form I, and the crystal Form I has at least an X-ray powder diffraction pattern with characteristic peaks represented by 2θ° of 7.83±0.2, 26.64±0.2, and 18.89±0.2.

2. The crystal polymorph of potassium N-[8-(2-hydroxybenzoyl)amino]octanoate according to item 1, characterized in that the crystal Form I further has at least an X-ray powder diffraction pattern with characteristic peaks represented by 2θ° of 5.24±0.2 or 21.59±0.2.

3. The crystal polymorph of potassium N-[8-(2-hydroxybenzoyl)amino]octanoate according to item 2, characterized in that the crystal Form I further has at least an X-ray powder diffraction pattern with characteristic peaks represented by 2θ° of 13.02±0.2 or 24.29±0.2.

4. The crystal polymorph of potassium N-[8-(2-hydroxybenzoyl)amino]octanoate according to item 3, characterized in that the crystal Form I further has at least an X-ray powder diffraction pattern with characteristic peaks represented by 2θ° of any one of 6.61±0.2, 10.43±0.2, 31.63±0.2, and 37.00±0.2.

5. The crystal polymorph of potassium N-[8-(2-hydroxybenzoyl)amino]octanoate according to any one of items 1-4, characterized in that the X-ray powder diffraction pattern of the crystal Form I is shown as FIG. 1.

6. The crystal polymorph of potassium N-[8-(2-hydroxybenzoyl)amino]octanoate according to any one of items 1-4, characterized in that the melting point of the crystal Form I is 163.1° C.

7. The crystal polymorph of potassium N-[8-(2-hydroxybenzoyl)amino]octanoate according to any one of items 1-4, characterized in that the adsorption water removal temperature of the crystal Form I is 83.6° C.

8. The crystal polymorph of potassium N-[8-(2-hydroxybenzoyl)amino]octanoate according to any one of items 1-4, characterized in that the crystal Form I loses 3.0% of weight at 140° C.

9. A crystal polymorph of potassium N-[8-(2-hydroxybenzoyl)amino]octanoate, characterized in that the crystal polymorph of potassium N-[8-(2-hydroxybenzoyl)amino] octanoate is crystal Form II, and the crystal Form II has at least an X-ray powder diffraction pattern with characteristic peaks represented by 2θ° of 24.76±0.2, 6.73±0.2, and 20.26±0.2.

10. The crystal polymorph of potassium N-[8-(2-hydroxybenzoyl)amino]octanoate according to item 9, characterized in that the crystal Form II further has at least an X-ray powder diffraction pattern with characteristic peaks represented by 2θ° of 14.68±0.2 or 25.55±0.2.

11. The crystal polymorph of potassium N-[8-(2-hydroxybenzoyl)amino]octanoate according to item 10, characterized in that the crystal Form II further has at least an X-ray powder diffraction pattern with characteristic peaks represented by 2θ° of 13.41±0.2 or 26.66±0.2.

12. The crystal polymorph of potassium N-[8-(2-hydroxybenzoyl)amino]octanoate according to item 11, characterized in that the crystal Form II further has at least an X-ray powder diffraction pattern with characteristic peaks represented by 2θ° of any one of 21.08±0.2, 25.79±0.2, 28.47±0.2, 12.07±0.2, 15.38±0.2, 23.38±0.2, 29.48±0.2, 22.55±0.2, 27.79±0.2, and 8.91±0.2.

13. The crystal polymorph of potassium N-[8-(2-hydroxybenzoyl)amino]octanoate according to item 9, characterized in that the X-ray powder diffraction pattern of the crystal Form II is shown as FIG. 3.

14. The crystal polymorph of potassium N-[8-(2-hydroxybenzoyl)amino]octanoate according to any one of items 9-13, characterized in that the melting point of the crystal Form II is 162.5° C.

15. The crystal polymorph of potassium N-[8-(2-hydroxybenzoyl)amino]octanoate according to any one of items 9-13, characterized in that the adsorption water removal temperature of the crystal Form II is 93° C.

16. The crystal polymorph of potassium N-[8-(2-hydroxybenzoyl)amino]octanoate according to any one of items 9-13, characterized in that the crystal Form II loses 5.6% of weight at 140° C.

17. A crystal polymorph of potassium N-[8-(2-hydroxybenzoyl)amino]octanoate, characterized in that the crystal polymorph of potassium N-[8-(2-hydroxybenzoyl)amino]octanoate is crystal Form III, and the crystal Form III has at least an X-ray powder diffraction pattern with characteristic peaks represented by 2θ° of 9.06±0.2, 23.30±0.2, and 21.44±0.2.

18. The crystal polymorph of potassium N-[8-(2-hydroxybenzoyl)amino]octanoate according to item 17, characterized in that the crystal Form III further has at least an X-ray powder diffraction pattern with characteristic peaks represented by 2θ° of 24.75±0.2 or 6.03±0.2.

19. The crystal polymorph of potassium N-[8-(2-hydroxybenzoyl)amino]octanoate according to item 18, characterized in that the crystal Form III further has at least an X-ray powder diffraction pattern with characteristic peaks represented by 2θ° of 21.20±0.2 or 17.06±0.2.

20. The crystal polymorph of potassium N-[8-(2-hydroxybenzoyl)amino]octanoate according to item 19, characterized in that the crystal Form III further has at least an X-ray powder diffraction pattern with characteristic peaks represented by 2θ° of any one of 21.75±0.2, 29.52±0.2, 22.15±0.2, 15.11±0.2, 28.47±0.2, 22.54±0.2, 30.71±0.2, 17.91±0.2, 15.64±0.2, and 26.49±0.2.

21. The crystal polymorph of potassium N-[8-(2-hydroxybenzoyl)amino]octanoate according to item 17, characterized in that the X-ray powder diffraction pattern of the crystal Form III is shown as FIG. 5.

22. The crystal polymorph of potassium N-[8-(2-hydroxybenzoyl)amino]octanoate according to any one of items 17-21, characterized in that the melting point of the crystal Form III is 162.0° C.

23. The crystal polymorph of potassium N-[8-(2-hydroxybenzoyl)amino]octanoate according to any one of items 17-21, characterized in that the adsorption water removal temperature of the crystal Form III is 94.5° C.

24. The crystal polymorph of potassium N-[8-(2-hydroxybenzoyl)amino]octanoate according to any one of items 17-21, characterized in that the crystal Form III loses 6.1% of weight at 140° C.

25. A crystal polymorph of potassium N-[8-(2-hydroxybenzoyl)amino]octanoate, characterized in that the crystal polymorph of potassium N-[8-(2-hydroxybenzoyl)amino]octanoate is crystal Form IV, and the crystal Form IV has at least an X-ray powder diffraction pattern with characteristic peaks represented by 2θ° of 16.25±0.2, 6.8±0.2, and 22.08±0.2.

26. The crystal polymorph of potassium N-[8-(2-hydroxybenzoyl)amino]octanoate according to item 25, characterized in that the crystal Form IV further has at least an X-ray powder diffraction pattern with characteristic peaks represented by 2θ° of 13.16±0.2 or 19.39±0.2.

27. The crystal polymorph of potassium N-[8-(2-hydroxybenzoyl)amino]octanoate according to item 26, characterized in that the crystal Form IV further has at least an X-ray powder diffraction pattern with characteristic peaks represented by 2θ° of 18.35±0.2 or 9.68±0.2.

28. The crystal polymorph of potassium N-[8-(2-hydroxybenzoyl)amino]octanoate according to item 27, characterized in that the crystal Form IV further has at least an X-ray powder diffraction pattern with characteristic peaks represented by 2θ° of any one of 15.92±0.2, 11.71±0.2, 29.91±0.2, 23.04±0.2, 16.56±0.2, 23.5±0.2, 27.31±0.2, 19.74±0.2, 34.34±0.2, and 18.82±0.2.

29. The crystal polymorph of potassium N-[8-(2-hydroxybenzoyl)amino]octanoate according to item 25, characterized in that the X-ray powder diffraction pattern of the crystal Form IV is shown as FIG. 7.

30. The crystal polymorph of potassium N-[8-(2-hydroxybenzoyl)amino]octanoate according to any one of items 25-29, characterized in that the melting point of the crystal Form IV is 163.8° C.

31. The crystal polymorph of potassium N-[8-(2-hydroxybenzoyl)amino]octanoate according to any one of items 25-29, characterized in that the adsorption water removal temperature of the crystal Form IV is 96.1° C.

32. The crystal polymorph of potassium N-[8-(2-hydroxybenzoyl)amino]octanoate according to any one of items 25-29, characterized in that the crystal Form IV loses 8.21% of weight at 150° C.

33. A preparation method of a crystal polymorph of potassium N-[8-(2-hydroxybenzoyl)amino]octanoate, characterized in that it comprises the steps of:

adding an organic solvent into a reaction vessel and stirring, then adding N-[8-(2-hydroxybenzoyl)amino]octanoic acid to stir evenly, adding potassium hydroxide solution dropwise, after the dropwise addition, concentrating to obtain the crude product;

adding an organic solvent to the crude product to obtain a filter cake after beating and suction filtration, rinsing the filter cake and placing it in a drying oven for drying to obtain the crystal polymorph of potassium N-[8-(2-hydroxybenzoyl)amino]octanoate.

34. The preparation method according to item 33, characterized in that the filter cake is rinsed and then put into a drying oven for drying to obtain crystal Form I of potassium N-[8-(2-hydroxybenzoyl)amino]octanoate, wherein the drying temperature is 60-100° C., and the drying time is 30-40 h; preferably, the drying is divided into two steps, firstly drying at 60° C. for 16 hours, and then drying again at 100° C. for 24 hours after pressure of the system is balanced with nitrogen;

the crystal Form I is crystal Form I of potassium N-[8-(2-hydroxybenzoyl)amino]octanoate according to any one of items 1-8.

35. The preparation method according to item 33, characterized in that the filter cake is prepared into uniform particles, and then the particles are placed in the drying oven for drying, and the dried particles are evenly spread in a 2-8° C. low temperature environment with a controlled relative humidity of 50% to keep for 2 days to produce crystal Form III of potassium N-[8-(2-hydroxybenzoyl)amino]octanoate.

36. The preparation method according to item 35, characterized in that as for drying the particles in the drying oven, the drying temperature is 60-100° C., and the drying time is 30-40 hours;

preferably, the drying is divided into two steps, firstly drying at 60° C. for 16 hours, and then drying again at 100° C. for 24 hours after pressure of the system is balanced with nitrogen.

37. The preparation method according to item 35, characterized in that the filter cake is made to pass through a 20-24 mesh sieve to obtain uniform particles;

the crystal Form III is the crystal Form III of potassium N-[8-(2-hydroxybenzoyl)amino]octanoate according to any one of items 17-24.

38. The preparation method according to any one of items 33-37, characterized in that the organic solvent is isopropanol or acetone.

39. The preparation method according to any one of items 33-37, characterized in that the concentration of the potassium hydroxide solution is 40-90%, preferably 50%.

40. The preparation method according to any one of items 33-37, characterized in that after adding N-[8-(2-hydroxybenzoyl)amino]octanoic acid, the temperature of the system is raised to 48° C. or above, then potassium hydroxide solution is added dropwise, and after the dropwise addition the temperature is maintained to react for 0.5-2 h;

preferably, after adding N-[8-(2-hydroxybenzoyl)amino]octanoic acid, the temperature of the system is raised to 48-52° C., then potassium hydroxide solution is added dropwise, and after the dropwise addition the temperature is maintained to react for 1 h.

41. The preparation method according to any one of items 33-37, characterized in that the N-[8-(2-hydroxybenzoyl)amino]octanoic acid and potassium hydroxide solution is added in a molar ratio of 1:1.

42. The preparation method according to any one of items 33-37, characterized in that the beating time after adding the organic solvent to the crude product is 0.5-1.5 hours, preferably 1 hour.

43. A preparation method of crystal Form I of potassium N-[8-(2-hydroxybenzoyl)amino]octanoate, characterized in that the crystal forms of potassium N-[8-(2-hydroxybenzoyl)amino]octanoate other than crystal Form I are heated to at least 75° C. to produce crystal Form I.

44. The preparation method according to item 43, characterized in that the crystal forms of potassium N-[8-(2-hydroxybenzoyl)amino]octanoate other than crystal Form I are at least one or more of crystal Form II, crystal Form III and crystal Form IV.

45. The preparation method according to item 43, characterized in that the crystal Forms of potassium N-[8-(2-hydroxybenzoyl)amino]octanoate other than crystal Form I are heated to 75° C. or above under nitrogen protection to produce crystal Form I of potassium N-[8-(2-hydroxybenzoyl)amino]octanoate.

46. The preparation method according to item 43, characterized in that the crystal Form II of potassium N-[8-(2-hydroxybenzoyl)amino]octanoate is heated to 140° C. under nitrogen protection to produce crystal Form I of potassium N-[8-(2-hydroxybenzoyl)amino]octanoate.

47. The preparation method according to item 43, characterized in that the crystal Form IV of potassium N-[8-(2-hydroxybenzoyl)amino]octanoate is heated to 110° C. under nitrogen protection to produce crystal Form I of potassium N-[8-(2-hydroxybenzoyl)amino]octanoate.

48. A preparation method of crystal Form I of potassium N-[8-(2-hydroxybenzoyl)amino]octanoate, characterized in that the crystal forms of potassium N-[8-(2-hydroxybenzoyl)amino]octanoate other than crystal Form I are lyophilized to produce crystal Form I.

49. The preparation method according to item 48, characterized in that the crystal forms of potassium N-[8-(2-hydroxybenzoyl)amino]octanoate other than crystal Form I are at least one or more of crystal Form II, crystal Form III and crystal Form IV.

50. The preparation method according to any one of items 43-49, characterized in that the crystal Form I is crystal Form I of potassium N-[8-(2-hydroxybenzoyl)amino]octanoate according to any one of items 1-8.

51. A preparation method of crystal Form II of potassium N-[8-(2-hydroxybenzoyl)amino]octanoate, characterized in that the crystal forms of potassium N-[8-(2-hydroxybenzoyl)amino]octanoate other than crystal Form II are exposed to an environment with 0-60% relative humidity at room temperature for 24 hours or more to produce crystal Form II of potassium N-[8-(2-hydroxybenzoyl)amino]octanoate.

52. The preparation method according to item 51, characterized in that environment has 20%, 30%, 40%, or 60% relative humidity.

53. The preparation method according to item 51, characterized in that the crystal forms of potassium N-[8-(2-hydroxybenzoyl)amino]octanoate other than crystal Form II are at least one or more of crystal Form I, crystal Form III and crystal Form IV.

54. The preparation method according to any one of items 51-53, characterized in that the crystal Form II is crystal Form II of potassium N-[8-(2-hydroxybenzoyl)amino]octanoate according to any one of items 9-16.

55. A preparation method of crystal Form IV of potassium N-[8-(2-hydroxybenzoyl)amino]octanoate, characterized in that it comprises the steps of: the crystal forms of potassium N-[8-(2-hydroxybenzoyl)amino]octanoate other than crystal Form IV are placed in an environment with higher than 80% relative humidity to form a gel-like substance;

the gel-like substance is exposed to an environment with 20-40% relative humidity at room temperature for 120 hours or more to produce crystal Form IV.

56. The preparation method according to item 55, characterized in that the crystal forms of potassium N-[8-(2-hydroxybenzoyl)amino]octanoate other than crystal Form IV are at least one or more of crystal Form I, crystal Form II and crystal Form III.

57. The preparation method according to item 55, characterized in that the gel-like substance is exposed to an environment with 20%, 30%, or 40% relative humidity, preferably 40% relative humidity.

58. The preparation method according to any one of items 55-57, characterized in that the crystal Form IV is crystal Form IV of potassium N-[8-(2-hydroxybenzoyl)amino]octanoate according to any one of items 25-32.

59. A pharmaceutical composition, characterized in that it comprises crystal polymorph of potassium N-[8-(2-hydroxybenzoyl)amino]octanoate.

60. The pharmaceutical composition according to item 59, characterized in that the crystal polymorph of potassium N-[8-(2-hydroxybenzoyl)amino]octanoate is one or more of crystal Form I, crystal Form II, crystal Form III and crystal Form IV.

61. The pharmaceutical composition according to any one of items 59-60, characterized in that it further comprises a preventive and/or therapeutic drug.

62. The pharmaceutical composition according to item 61, characterized in that in the pharmaceutical composition, the weight ratio of crystal polymorph of potassium N-[8-(2-hydroxybenzoyl)amino]octanoate to the preventive and/or therapeutic drugs is (20-60):1, preferably 30:1.

63. The pharmaceutical composition according to item 62, characterized in that the preventive and/or therapeutic drugs are glucagon-like peptide-1, insulin, PYY (peptide YY), human amylin, heparin, human growth hormone, interferon, monoclonal antibody, protease inhibitor, and thrombopoietin.

64. Use of a crystal polymorph of potassium N-[8-(2-hydroxybenzoyl)amino]octanoate or a pharmaceutical composition thereof in the preparation of a preventive and/or therapeutic medicament.

65. Use of a crystal polymorph of potassium N-[8-(2-hydroxybenzoyl)amino]octanoate or a pharmaceutical composition thereof in the promotion of drug delivery.

66. Use of a crystal polymorph of potassium N-[8-(2-hydroxybenzoyl)amino]octanoate or a pharmaceutical composition thereof in the preparation of a medicament for preventing and/or treating diabetes, or diabetic complications, or reducing body weight.

There are four forms for the crystal polymorph of potassium N-[8-(2-hydroxybenzoyl)amino]octanoate provided in this application, which have high solubility and strong stability, can deliver drugs more effectively, and increase the permeability of the delivered drugs in the gastrointestinal tract, and are conducive to the preparation of oral preparations, so that the preventive and/or therapeutic drugs can be better delivered into the body to achieve the effect of improving bioavailability.

BRIEF DESCRIPTION OF THE DRAWINGS

The accompanying drawings are used for a better understanding of the present application, and do not constitute an improper limitation of the present application, wherein.

DETAILED DESCRIPTION OF THE APPLICATION

Figure 1:
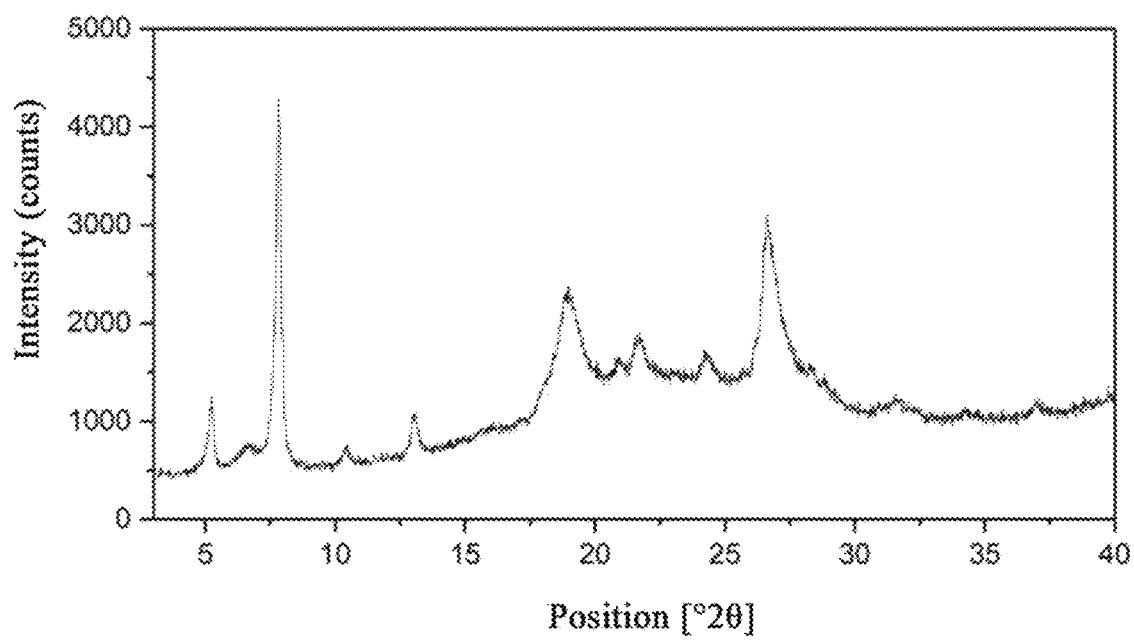
FIG. 1 is an X-ray powder diffraction pattern of the crystal Form I of PNAC prepared in Example 1.

Exemplary embodiments of the present application are described below with reference to the accompanying drawings, which include various details of the embodiments of the present application to facilitate understanding and should be considered as exemplary only. Accordingly, those of ordinary skill in the art will recognize that various changes and modifications of the embodiments described herein can be made without departing from the scope and spirit of the present application. In the case of not conflicting with the definitions in this specification, the terms in this specification have the meanings commonly understood by those skilled in the art, but in case of conflict, the definitions in this specification shall prevail.

Potassium N-[8-(2-hydroxybenzoyl)amino]octanoate (PNAC for short), as shown in Formula (III):

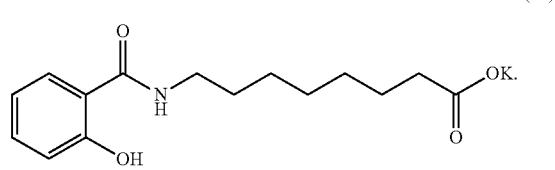

Formula (III)

X-Ray Powder Diffraction

X-Ray Powder Diffraction (XRPD) is usually applied to the analysis of crystal structure. X-rays are electromagnetic waves that generate a periodically changing electromagnetic field in a crystal when they are incident on it. X-rays cause electrons and nuclei in atoms to vibrate, and the vibrations in a nucleus are ignored due to the large mass of the nucleus. The vibrating electrons are the source of secondary X-rays with the same wavelength and phase as the incident light. Based on the periodicity of the crystal structure, the scattered waves of each electron in the crystal interfere with each other and superimpose each other, and this is called diffraction. The direction in which the scattered wave phases are consistent and mutually reinforcing is called the diffraction direction, resulting in diffraction rays.

Instrument model: PANalytical Empyrean and X'Pert3 ray powder diffraction analyzer;
Ray: Monochromatic Cu-Kα ray (λ=1.5406);
Scanning mode: θ/2θ, scanning range: 2-40°;
Voltage: 40 KV, Current: 40 mA.

Thermogravimetric Analysis

Thermogravimetric Analysis (TGA) refers to a thermal analysis technique that measures the relationship between the mass of the sample to be tested and the temperature change at a program controlled temperature, and is used to study the thermal stability and composition of materials. TGA is a commonly used detection method in R&D and quality control. Thermogravimetric analysis is often used in combination with other analysis methods in actual material analysis, to conduct comprehensive thermal analysis and analyze materials comprehensively and accurately. The curve recorded by the thermogravimetric analyzer is called TGA curve.

Instrument model: TA Q5000/Discovery 5500;
Purge gas: nitrogen;
Heating mold: linear heating;
Temperature range: from room temperature to 350° C.

Differential Scanning Calorimetry

Differential scanning calorimetry (DSC) is a technique that measures the rate of heat flow of a sample relative to a reference as a function of temperature or time under control of temperature program. The curve recorded by the differential scanning calorimeter is called DSC curve. Generally, W/g or mW/mg (i.e., the power flowing to each gram of the sample) is the ordinate, and the temperature T or time t is the abscissa. The differential scanning calorimeter may be used to measure various thermodynamic and kinetic parameters, such as specific heat capacity, heat of reaction, heat of transition, phase diagram, reaction rate, crystallization rate, polymer crystallinity, sample purity, etc. This method has a wide temperature range (−175° C. to 725° C.), high resolution and less sample consumption. It is suitable for analysis of inorganic substances, organic compounds and pharmaceuticals.

Instrument model: TAQ2000/Discovery 2500;
Purge gas: nitrogen;
Heating mold: linear heating;
Temperature range: 25-300° C.

The present application provides a crystal polymorph of potassium N-[8-(2-hydroxybenzoyl)amino]octanoate, wherein the crystal polymorph of potassium N-[8-(2-hydroxybenzoyl)amino]octanoate is crystal Form I, and the crystal Form I has an X-ray powder diffraction pattern with characteristic peaks represented by 2θ° of 7.83±0.2, 26.64±0.2, and 18.89±0.2.

In the present application, the crystal Form I has an X-ray powder diffraction pattern with characteristic peaks represented by 2θ° of 7.83±0.2, 26.64±0.2, 18.89±0.2, and 5.24±0.2.

In the present application, the crystal Form I has an X-ray powder diffraction pattern with characteristic peaks represented by 2θ° of 7.83±0.2, 26.64±0.2, 18.89±0.2, and 21.59±0.2.

In the present application, the crystal Form I has an X-ray powder diffraction pattern with characteristic peaks represented by 2θ° of 7.83±0.2, 26.64±0.2, 18.89±0.2, 5.24±0.2, and 21.59±0.2.

In the present application, the crystal Form I has an X-ray powder diffraction pattern with characteristic peaks represented by 2θ° of 7.83±0.2, 26.64±0.2, 18.89±0.2, 5.24±0.2, 21.59±0.2, and 24.29±0.2.

In the present application, the crystal Form I has an X-ray powder diffraction pattern with characteristic peaks represented by 2θ° of 7.83±0.2, 26.64±0.2, 18.89±0.2, 5.24±0.2, 21.59±0.2, and 13.02±0.2.

In the present application, the crystal Form I has X-ray powder diffraction pattern with characteristic peaks represented by 2θ° of 7.83±0.2, 26.64±0.2, 18.89±0.2, 5.24±0.2, 21.59±0.2, 13.02±0.2, and 24.29±0.2.

In the present application, the crystal Form I has X-ray powder diffraction pattern with characteristic peaks represented by 2θ° of 7.83±0.2, 26.64±0.2, 18.89±0.2, 5.24±0.2, 21.59±0.2, 13.02±0.2, 24.29±0.2, and 6.61±0.2.

In the present application, the crystal Form I has X-ray powder diffraction pattern with characteristic peaks represented by 2θ° of: 7.83±0.2, 26.64±0.2, 18.89±0.2, 5.24±0.2, 21.59±0.2, 13.02±0.2, 24.29±0.2, 6.61±0.2, and 10.43±0.2.

In the present application, the crystal Form I has X-ray powder diffraction pattern with characteristic peaks represented by 2θ° of: 7.83±0.2, 26.64±0.2, 18.89±0.2, 5.24±0.2, 21.59±0.2, 13.02±0.2, 24.29±0.2, 6.61±0.2, 10.43±0.2, and 31.63±0.2.

In the present application, the crystal Form I has X-ray powder diffraction pattern with characteristic peaks represented by 2θ° of: 7.83±0.2, 26.64±0.2, 18.89±0.2, 5.24±0.2, 21.59±0.2, 13.02±0.2, 24.29±0.2, 6.61±0.2, 10.43±0.2, 31.63±0.2, and 37.00±0.2.

In the present application, the X-ray powder diffraction pattern of the crystal Form I is shown as FIG. 1.

In this application, the melting point of the crystal Form I is 163.1° C.

In the present application, the adsorption water removal temperature of the crystal Form I is 83.6° C.

In the present application, the crystal Form I loses 3.0% of weight at 140° C.

The present application provides a crystal polymorph of potassium N-[8-(2-hydroxybenzoyl)amino]octanoate, wherein the crystal polymorph of potassium N-[8-(2-hydroxybenzoyl)amino]octanoate is crystal Form II, and the crystal Form II has at least an X-ray powder diffraction pattern with characteristic peaks represented by 2θ° of 24.76±0.2, 6.73±0.2, and 20.26±0.2.

In the present application, the crystal Form II has an X-ray powder diffraction pattern with characteristic peaks represented by 2θ° of 24.76±0.2, 6.73±0.2, 20.26±0.2, and 14.68±0.2.

In the present application, the crystal Form II has an X-ray powder diffraction pattern with characteristic peaks represented by 2θ° of 24.76±0.2, 6.73±0.2, 20.26±0.2, and 25.55±0.2.

In the present application, the crystal Form II has an X-ray powder diffraction pattern with characteristic peaks represented by 2θ° of 24.76±0.2, 6.73±0.2, 20.26±0.2, 14.68±0.2, and 25.55±0.2.

In the present application, the crystal Form II has an X-ray powder diffraction pattern with characteristic peaks represented by 2θ° of 24.76±0.2, 6.73±0.2, 20.26±0.2, 14.68±0.2, 25.55±0.2, and 13.41±0.2.

In the present application, the crystal Form II has an X-ray powder diffraction pattern with characteristic peaks represented by 2θ° of 24.76±0.2, 6.73±0.2, 20.26±0.2, 14.68±0.2, 25.55±0.2, and 26.66±0.2.

In the present application, the crystal Form II has an X-ray powder diffraction pattern with characteristic peaks represented by 2θ° of 24.76±0.2, 6.73±0.2, 20.26±0.2, 14.68±0.2, 25.55±0.2, 13.41±0.2, and 26.66±0.2.

In the present application, the crystal Form II has an X-ray powder diffraction pattern with characteristic peaks represented by 2θ° of 24.76±0.2, 6.73±0.2, 20.26±0.2, 14.68±0.2, 25.55±0.2, 13.41±0.2, 26.66±0.2, and 21.08±0.2.

In the present application, the crystal Form II has an X-ray powder diffraction pattern with characteristic peaks represented by 2θ° of 24.76±0.2, 6.73±0.2, 20.26±0.2, 14.68±0.2, 25.55±0.2, 13.41±0.2, 26.66±0.2, 21.08±0.2, and 25.79±0.2.

In the present application, the crystal Form II has an X-ray powder diffraction pattern with characteristic peaks represented by 2θ° of 24.76±0.2, 6.73±0.2, 20.26±0.2, 14.68±0.2, 25.55±0.2, 13.41±0.2, 26.66±0.2, 21.08±0.2, 25.79±0.2, and 28.47±0.2.

In the present application, the crystal Form II has an X-ray powder diffraction pattern with characteristic peaks represented by 2θ° of 24.76±0.2, 6.73±0.2, 20.26±0.2, 14.68±0.2, 25.55±0.2, 13.41±0.2, 26.66±0.2, 21.08±0.2, 25.79±0.2, 28.47±0.2, and 12.07±0.2.

In the present application, the crystal Form II has an X-ray powder diffraction pattern with characteristic peaks represented by 2θ° of 24.76±0.2, 6.73±0.2, 20.26±0.2, 14.68±0.2, 25.55±0.2, 13.41±0.2, 26.66±0.2, 21.08±0.2, 25.79±0.2, 28.47±0.2, 12.07±0.2, and 15.38±0.2.

In the present application, the crystal Form II has an X-ray powder diffraction pattern with characteristic peaks represented by 2θ° of 24.76±0.2, 6.73±0.2, 20.26±0.2, 14.68±0.2, 25.55±0.2, 13.41±0.2, 26.66±0.2, 21.08±0.2, 25.79±0.2, 28.47±0.2, 12.07±0.2, 15.38±0.2, and 23.38±0.2.

In the present application, the crystal Form II has an X-ray powder diffraction pattern with characteristic peaks represented by 2θ° of 24.76±0.2, 6.73±0.2, 20.26±0.2, 14.68±0.2, 25.55±0.2, 13.41±0.2, 26.66±0.2, 21.08±0.2, 25.79±0.2, 28.47±0.2, 12.07±0.2, 15.38±0.2, 23.38±0.2, and 29.48±0.2.

In the present application, the crystal Form II has an X-ray powder diffraction pattern with characteristic peaks represented by 2θ° of 24.76±0.2, 6.73±0.2, 20.26±0.2, 14.68±0.2, 25.55±0.2, 13.41±0.2, 26.66±0.2, 21.08±0.2, 25.79±0.2, 28.47±0.2, 12.07±0.2, 15.38±0.2, 23.38±0.2, 29.48±0.2, and 22.55±0.2.

In the present application, the crystal Form II has an X-ray powder diffraction pattern with characteristic peaks represented by 2θ° of 24.76±0.2, 6.73±0.2, 20.26±0.2, 14.68±0.2, 25.55±0.2, 13.41±0.2, 26.66±0.2, 21.08±0.2, 25.79±0.2, 28.47±0.2, 12.07±0.2, 15.38±0.2, 23.38±0.2, 29.48±0.2, 22.55±0.2, and 27.79±0.2.

In the present application, the crystal Form II has an X-ray powder diffraction pattern with characteristic peaks represented by 2θ° of 24.76±0.2, 6.73±0.2, 20.26±0.2, 14.68±0.2, 25.55±0.2, 13.41±0.2, 26.66±0.2, 21.08±0.2, 25.79±0.2, 28.47±0.2, 12.07±0.2, 15.38±0.2, 23.38±0.2, 29.48±0.2, 22.55±0.2, 27.79±0.2, and 8.91±0.2.

Figure 3:
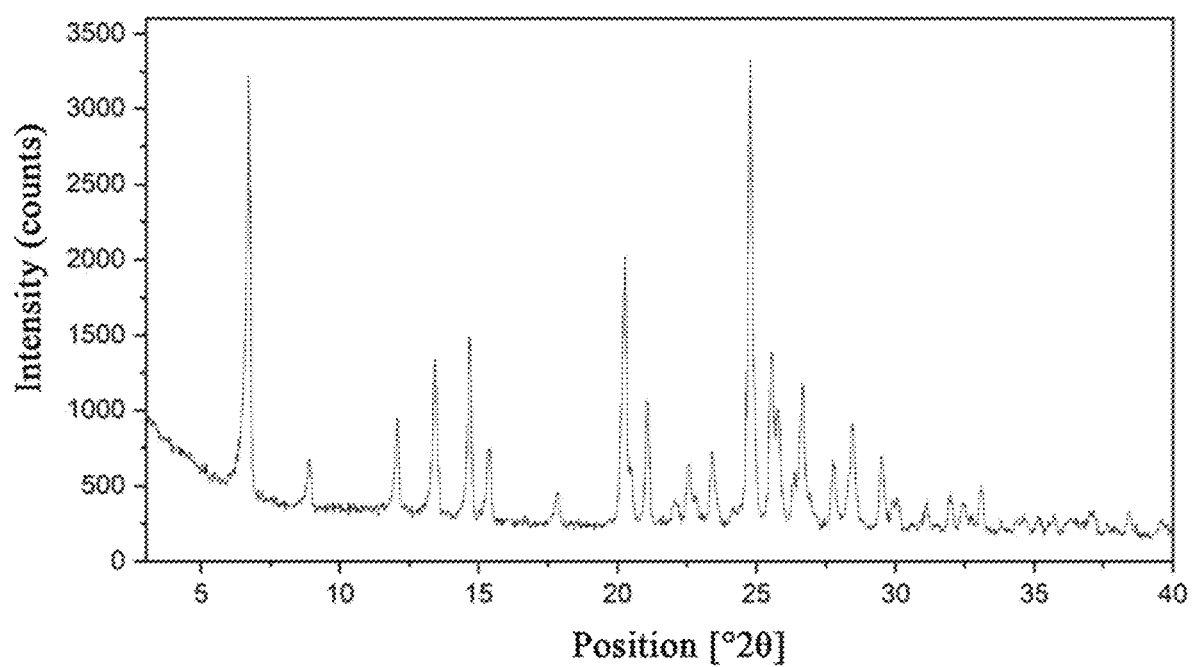
FIG. 3 is an X-ray powder diffraction pattern of the crystal Form II of PNAC prepared in Example 2.

In the present application, the X-ray powder diffraction pattern of the crystal Form II is shown as FIG. 3.

In the present application, the melting point of the crystal Form II is 162.5° C.

In the present application, the adsorption water removal temperature of the crystal Form II is 93° C.

In the present application, the crystal Form II loses 5.6% of weight at 140° C.

The present application provides a crystal polymorph of potassium N-[8-(2-hydroxybenzoyl)amino]octanoate, wherein the crystal polymorph of potassium N-[8-(2-hydroxybenzoyl)amino]octanoate is crystal Form III, and the crystal Form III has at least an X-ray powder diffraction pattern with characteristic peaks represented by 2θ° of 9.06±0.2, 23.30±0.2, and 21.44±0.2.

In the present application, the crystal Form III has an X-ray powder diffraction pattern with characteristic peaks represented by 2θ° of 9.06±0.2, 23.30±0.2, 21.44±0.2, and 24.75±0.2.

In the present application, the crystal Form III has an X-ray powder diffraction pattern with characteristic peaks represented by 2θ° of 9.06±0.2, 23.30±0.2, 21.44±0.2, and 6.03±0.2.

In the present application, the crystal Form III has an X-ray powder diffraction pattern with characteristic peaks represented by 2θ° of 9.06±0.2, 23.30±0.2, 21.44±0.2, 24.75±0.2, and 6.03±0.2.

In the present application, the crystal Form III has an X-ray powder diffraction pattern with characteristic peaks represented by 2θ° of 9.06±0.2, 23.30±0.2, 21.44±0.2, 24.75±0.2, 6.03±0.2, and 21.20±0.2.

In the present application, the crystal Form III has an X-ray powder diffraction pattern with characteristic peaks represented by 2θ° of 9.06±0.2, 23.30±0.2, 21.44±0.2, 24.75±0.2, 6.03±0.2, and 17.06±0.2.

In the present application, the crystal Form III has an X-ray powder diffraction pattern with characteristic peaks represented by 2θ° of 9.06±0.2, 23.30±0.2, 21.44±0.2, 24.75±0.2, 6.03±0.2, 21.20±0.2, and 17.06±0.2.

In the present application, the crystal Form III has an X-ray powder diffraction pattern with characteristic peaks represented by 2θ° of 9.06±0.2, 23.30±0.2, 21.44±0.2, 24.75±0.2, 6.03±0.2, 21.20±0.2, 17.06±0.2, and 21.75±0.2.

In the present application, the crystal Form III has an X-ray powder diffraction pattern with characteristic peaks represented by 2θ° of 9.06±0.2, 23.30±0.2, 21.44±0.2, 24.75±0.2, 6.03±0.2, 21.20±0.2, 17.06±0.2, 21.75±0.2, and 29.52±0.2.

In the present application, the crystal Form III has an X-ray powder diffraction pattern with characteristic peaks represented by 2θ° of 9.06±0.2, 23.30±0.2, 21.44±0.2, 24.75±0.2, 6.03±0.2, 21.20±0.2, 17.06±0.2, 21.75±0.2, 29.52±0.2, and 22.15±0.2.

In the present application, the crystal Form III has an X-ray powder diffraction pattern with characteristic peaks represented by 2θ° of: 9.06±0.2, 23.30±0.2, 21.44±0.2, 24.75±0.2, 6.03±0.2, 21.20±0.2, 17.06±0.2, 21.75±0.2, 29.52±0.2, 22.15±0.2, and 15.11±0.2.

In the present application, the crystal Form III has an X-ray powder diffraction pattern with characteristic peaks represented by 2θ° of 9.06±0.2, 23.30±0.2, 21.44±0.2, 24.75±0.2, 6.03±0.2, 21.20±0.2, 17.06±0.2, 21.75±0.2, 29.52±0.2, 22.15±0.2, 15.11±0.2, 28.47±0.2.

In the present application, the crystal Form III has an X-ray powder diffraction pattern with characteristic peaks represented by 2θ° of 9.06±0.2, 23.30±0.2, 21.44±0.2, 24.75±0.2, 6.03±0.2, 21.20±0.2, 17.06±0.2, 21.75±0.2, 29.52±0.2, 22.15±0.2, 15.11±0.2, 28.47±0.2, and 22.54±0.2.

In the present application, the crystal Form III has an X-ray powder diffraction pattern with characteristic peaks represented by 2θ° of 9.06±0.2, 23.30±0.2, 21.44±0.2, 24.75±0.2, 6.03±0.2, 21.20±0.2, 17.06±0.2, 21.75±0.2, 29.52±0.2, 22.15±0.2, 15.11±0.2, 28.47±0.2, 22.54±0.2, and 30.71±0.2.

In the present application, the crystal Form III has an X-ray powder diffraction pattern with characteristic peaks represented by 2θ° of 9.06±0.2, 23.30±0.2, 21.44±0.2, 24.75±0.2, 6.03±0.2, 21.20±0.2, 17.06±0.2, 21.75±0.2, 29.52±0.2, 22.15±0.2, 15.11±0.2, 28.47±0.2, 22.54±0.2, 30.71±0.2, and 17.91±0.2.

In the present application, the crystal Form III has an X-ray powder diffraction pattern with characteristic peaks represented by 2θ° of 9.06±0.2, 23.30±0.2, 21.44±0.2, 24.75±0.2, 6.03±0.2, 21.20±0.2, 17.06±0.2, 21.75±0.2, 29.52±0.2, 22.15±0.2, 15.11±0.2, 28.47±0.2, 22.54±0.2, 30.71±0.2, 17.91±0.2, and 15.64±0.2.

In the present application, the crystal Form III has an X-ray powder diffraction pattern with characteristic peaks represented by 2θ° of 9.06±0.2, 23.30±0.2, 21.44±0.2, 24.75±0.2, 6.03±0.2, 21.20±0.2, 17.06±0.2, 21.75±0.2, 29.52±0.2, 22.15±0.2, 15.11±0.2, 28.47±0.2, 22.54±0.2, 30.71±0.2, 17.91±0.2, 15.64±0.2, and 26.49±0.2.

Figure 5:
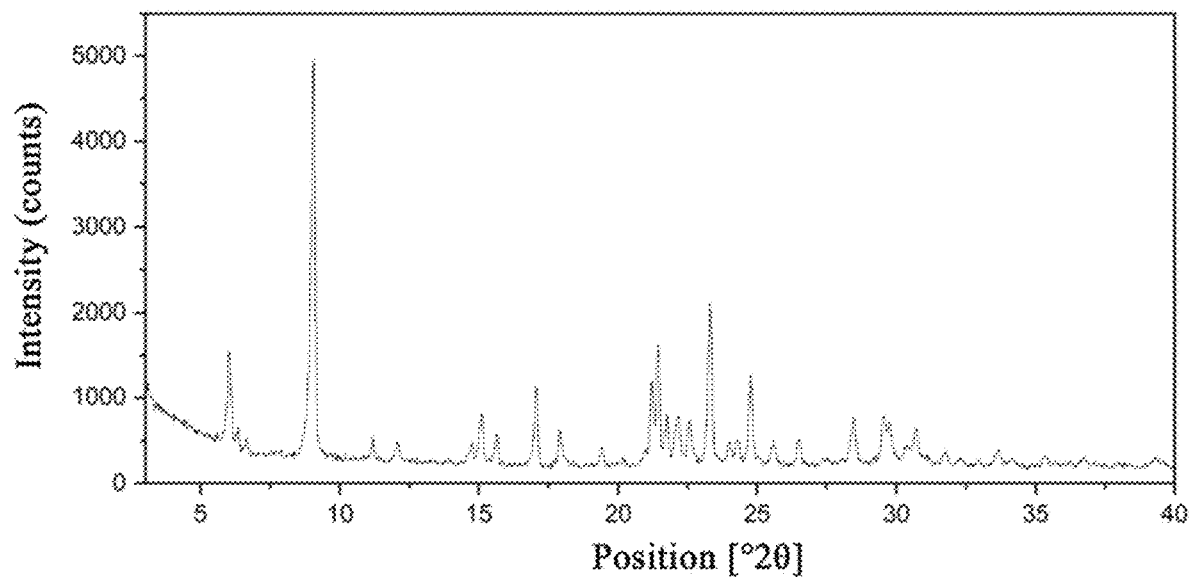
FIG. 5 is an X-ray powder diffraction pattern of the crystal Form III of PNAC prepared in Example 3.

In the present application, the X-ray powder diffraction pattern of the crystal Form III is shown as FIG. 5.

In this application, the melting point of the crystal Form III is 162.0° C.

In the present application, the adsorption water removal temperature of the crystal Form III is 94.5° C.

In the present application, the crystal Form III loses 6.1% of weight at 140° C.

The present application provides a crystal polymorph of potassium N-[8-(2-hydroxybenzoyl)amino]octanoate, wherein the crystal polymorph of potassium N-[8-(2-hydroxybenzoyl)amino]octanoate is crystal Form IV, and the crystal Form IV has at least an X-ray powder diffraction pattern with characteristic peaks represented by 2θ° of 16.25±0.2, 6.8±0.2, and 22.08±0.2.

In the present application, the crystal Form IV has an X-ray powder diffraction pattern with characteristic peaks represented by 2θ° of 16.25±0.2, 6.8±0.2, 22.08±0.2, and 13.16±0.2.

In the present application, the crystal Form IV has an X-ray powder diffraction pattern with characteristic peaks represented by 2θ° of 16.25±0.2, 6.8±0.2, 22.08±0.2, and 19.39±0.2.

In the present application, the crystal Form IV has an X-ray powder diffraction pattern with characteristic peaks represented by 2θ° of 16.25±0.2, 6.8±0.2, 22.08±0.2, 13.16±0.2, and 19.39±0.2.

In the present application, the crystal Form IV has an X-ray powder diffraction pattern with characteristic peaks represented by 2θ° of 16.25±0.2, 6.8±0.2, 22.08±0.2, 13.16±0.2, 19.39±0.2, and 18.35±0.2.

In the present application, the crystal Form IV has an X-ray powder diffraction pattern with characteristic peaks represented by 2θ° of 16.25±0.2, 6.8±0.2, 22.08±0.2, 13.16±0.2, 19.39±0.2, and 9.68±0.2.

In the present application, the crystal Form IV has an X-ray powder diffraction pattern with characteristic peaks represented by 2θ° of 16.25±0.2, 6.8±0.2, 22.08±0.2, 13.16±0.2, 19.39±0.2, 18.35±0.2, and 9.68±0.2.

In the present application, the crystal Form IV has an X-ray powder diffraction pattern with characteristic peaks represented by 2θ° of 16.25±0.2, 6.8±0.2, 22.08±0.2, 13.16±0.2, 19.39±0.2, 18.35±0.2, 9.68±0.2, and 15.92±0.2.

In the present application, the crystal Form IV has an X-ray powder diffraction pattern with characteristic peaks represented by 2θ° of 16.25±0.2, 6.8±0.2, 22.08±0.2, 13.16±0.2, 19.39±0.2, 18.35±0.2, 9.68±0.2, 15.92±0.2, and 11.71±0.2.

In the present application, the crystal Form IV has an X-ray powder diffraction pattern with characteristic peaks represented by 2θ° of 16.25±0.2, 6.8±0.2, 22.08±0.2, 13.16±0.2, 19.39±0.2, 18.35±0.2, 9.68±0.2, 15.92±0.2, 11.71±0.2, and 29.91±0.2.

In the present application, the crystal Form IV has an X-ray powder diffraction pattern with characteristic peaks represented by 2θ° of 16.25±0.2, 6.8±0.2, 22.08±0.2, 13.16±0.2, 19.39±0.2, 18.35±0.2, 9.68±0.2, 15.92±0.2, 11.71±0.2, 29.91±0.2, and 23.04±0.2.

In the present application, the crystal Form IV has an X-ray powder diffraction pattern with characteristic peaks represented by 2θ° of 16.25±0.2, 6.8±0.2, 22.08±0.2, 13.16±0.2, 19.39±0.2, 18.35±0.2, 9.68±0.2, 15.92±0.2, 11.71±0.2, 29.91±0.2, 23.04±0.2, and 16.56±0.2.

In the present application, the crystal Form IV has an X-ray powder diffraction pattern with characteristic peaks represented by 2θ° of 16.25±0.2, 6.8±0.2, 22.08±0.2, 13.16±0.2, 19.39±0.2, 18.35±0.2, 9.68±0.2, 15.92±0.2, 11.71±0.2, 29.91±0.2, 23.04±0.2, 16.56±0.2, 23.5±0.2.

In the present application, the crystal Form IV has an X-ray powder diffraction pattern with characteristic peaks represented by 2θ° of 16.25±0.2, 6.8±0.2, 22.08±0.2, 13.16±0.2, 19.39±0.2, 18.35±0.2, 9.68±0.2, 15.92±0.2, 11.71±0.2, 29.91±0.2, 23.04±0.2, 16.56±0.2, 23.5±0.2, and 27.31±0.2.

In the present application, the crystal Form IV has an X-ray powder diffraction pattern with characteristic peaks represented by 2θ° of 16.25±0.2, 6.8±0.2, 22.08±0.2, 13.16±0.2, 19.39±0.2, 18.35±0.2, 9.68±0.2, 15.92±0.2, 11.71±0.2, 29.91±0.2, 23.04±0.2, 16.56±0.2, 23.5±0.2, 27.31±0.2, and 19.74±0.2.

In the present application, the crystal Form IV has an X-ray powder diffraction pattern with characteristic peaks represented by 2θ° of 16.25±0.2, 6.8±0.2, 22.08±0.2, 13.16±0.2, 19.39±0.2, 18.35±0.2, 9.68±0.2, 15.92±0.2, 11.71±0.2, 29.91±0.2, 23.04±0.2, 16.56±0.2, 23.5±0.2, 27.31±0.2, 19.74±0.2, and 34.34±0.2.

In the present application, the crystal Form IV has an X-ray powder diffraction pattern with characteristic peaks represented by 2θ° of 16.25±0.2, 6.8±0.2, 22.08±0.2, 13.16±0.2, 19.39±0.2, 18.35±0.2, 9.68±0.2, 15.92±0.2, 11.71±0.2, 29.91±0.2, 23.04±0.2, 16.56±0.2, 23.5±0.2, 27.31±0.2, 19.74±0.2, 34.34±0.2, and 18.82±0.2.

Figure 7:
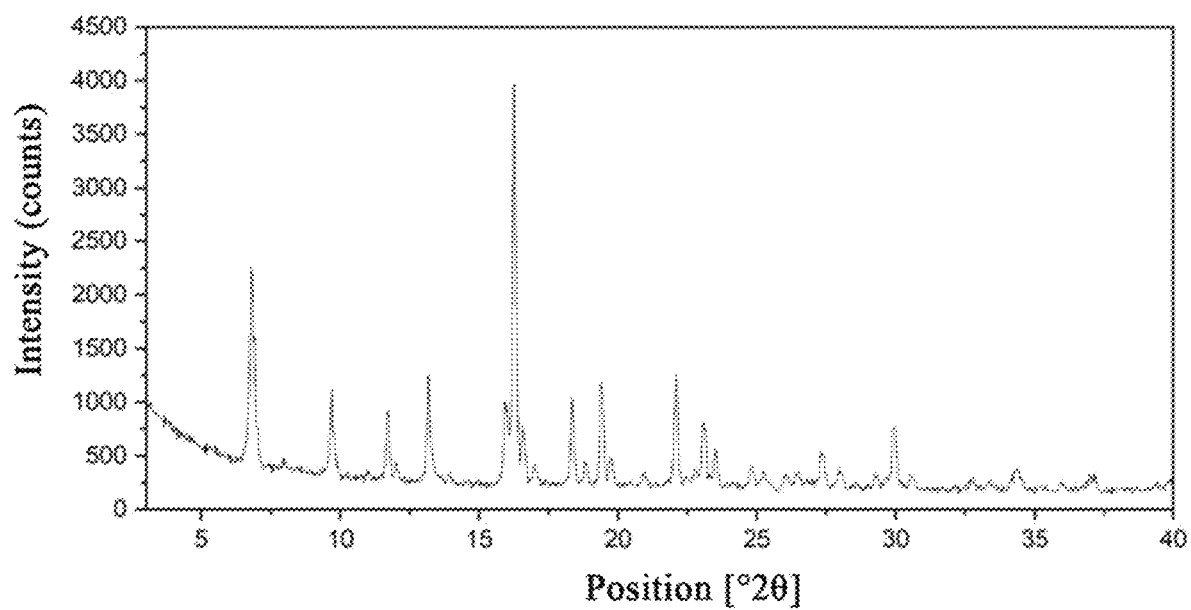
FIG. 7 is an X-ray powder diffraction pattern of the crystal Form IV of PNAC prepared in Example 4.

In the present application, the X-ray powder diffraction pattern of the crystal Form IV is shown as FIG. 7.

In the present application, the melting point of the crystal Form IV is 163.8° C.

In the present application, the adsorption water removal temperature of the crystal Form IV is 96.1° C.

In the present application, the crystal Form IV loses 8.21% of weight at 150° C.

The crystal forms I-IV of the PNAC provided by the present application all have good solubility, bioavailability and solid-state stability, particularly the crystal forms I and II have better bioavailability and solid-state stability.

The present application provides a preparation method of crystal Form I of potassium N-[8-(2-hydroxybenzoyl)amino]octanoate, which comprises the following steps:

step 1: adding an organic solvent to a reaction vessel and stirring, then adding N-[8-(2-hydroxybenzoyl)amino]octanoic acid to stir evenly, adding potassium hydroxide solution dropwise, after the dropwise addition, concentrating to obtain the crude product;

step 2: adding an organic solvent to the crude product to obtain a filter cake after beating and suction filtration, rinsing the filter cake and placing it in a drying oven for drying to obtain crystal Form I of potassium N-[8-(2-hydroxybenzoyl)amino]octanoate, wherein the drying temperature is 60-100° C., and the drying time is 30-40 h.

The drying temperature may be 60° C., 65° C., 70° C., 75° C., 80° C., 85° C., 90° C., 95° C., or 100° C.

The drying time may be 30 h, 31 h, 32 h, 33 h, 34 h, 35 h, 36 h, 37 h, 38 h, 39 h, or 40 hours.

Preferably, the drying is divided into two steps, firstly drying at 60° C. for 16 h, and then drying again at 100° C. for 24 h after pressure of the system is balanced with nitrogen.

In this application, the organic solvent is isopropanol or acetone.

In the present application, the concentration of the potassium hydroxide solution is 40-90%, preferably 50%.

The concentration of the potassium hydroxide solution may be 40%, 45%, 50%, 55%, 60%, 65%, 70%, 75%, 80%, 85%, or 90%.

In this application, after adding N-[8-(2-hydroxybenzoyl)amino]octanoic acid, the temperature of the system is raised to 48° C. or above, and then potassium hydroxide solution is added dropwise, and after the dropwise addition the temperature is maintained at 48° C. or above to react for 0.5 h-2 h.

Preferably, after adding N-[8-(2-hydroxybenzoyl)amino]octanoic acid, the temperature of the system is raised to 48-52° C., and then potassium hydroxide solution is added dropwise, and after the dropwise addition the temperature is maintained at 48-52° C. to react for 1 h.

The system temperature may be 48° C., 49° C., 50° C., 51° C., 52° C., 53° C., 54° C., or 55° C.

The reaction time at a maintained temperature may be 0.5 h, 0.6 h, 0.7 h, 0.8 h, 0.9 h, 1 h, 1.1 h, 1.2 h, 1.3 h, 1.4 h, 1.5 h, 1.6 h, 1.7 h, 1.8 h, 1.9 h, or 2 h.

In this application, the molar ratio of N-[8-(2-hydroxybenzoyl)amino]octanoic acid and potassium hydroxide is 1:1.

In the present application, the beating time after adding the organic solvent to the crude product is 0.5 h-1.5 h, preferably 1 h.

The beating time after adding the organic solvent to the crude product may be 0.5 h, 0.6 h, 0.7 h, 0.8 h, 0.9 h, 1 h, 1.1 h, 1.2 h, 1.3 h, 1.4 h, 1.5 h, 1.6 h, 1.7 h, 1.8 h, 1.9 h, or 2 h.

The present application provides a second preparation method of crystal Form I of potassium N-[8-(2-hydroxybenzoyl)amino]octanoate, wherein the crystal forms of potassium N-[8-(2-hydroxybenzoyl)amino]octanoate other than crystal Form I are heated to at least above 75° C. to produce crystal Form I.

In the present application, the crystal forms of potassium N-[8-(2-hydroxybenzoyl)amino]octanoate other than crystal Form I are at least one or more of crystal Form II, crystal Form III and crystal Form IV.

The crystal form of potassium N-[8-(2-hydroxybenzoyl)amino]octanoate other than crystal Form I may be crystal Form II.

The crystal form of potassium N-[8-(2-hydroxybenzoyl)amino]octanoate other than crystal Form I may be crystal Form III.

The crystal form of potassium N-[8-(2-hydroxybenzoyl)amino]octanoate other than crystal Form I may be crystal Form IV.

The crystal forms of potassium N-[8-(2-hydroxybenzoyl)amino]octanoate other than crystal Form I may be crystal Form II and crystal Form III.

The crystal forms of potassium N-[8-(2-hydroxybenzoyl)amino]octanoate other than crystal Form I may be crystal Form II and crystal Form IV.

The crystal forms of potassium N-[8-(2-hydroxybenzoyl)amino]octanoate other than crystal Form I may be crystal Form III and crystal Form IV.

The crystal forms of potassium N-[8-(2-hydroxybenzoyl)amino]octanoate other than crystal Form I may be crystal Form II, crystal Form III and crystal Form IV.

In the present application, the crystal Forms of potassium N-[8-(2-hydroxybenzoyl)amino]octanoate other than crystal Form I are heated to 75° C. or above under nitrogen protection to produce crystal Form I of potassium N-[8-(2-hydroxybenzoyl)amino]octanoate, wherein the heating time is 0-300 min.

The heating temperature is preferably 110-140° C. The heating temperature may be 110° C., 115° C., 120° C., 125° C., 130° C., 135° C., or 140° C.

The heating time may be 10 min, 15 min, 20 min, 25 min, 30 min, 35 min, 40 min, 45 min, 50 min, 55 min, 60 min, 65 min, 70 min, 75 min, 80 min, 85 min, 90 min, 95 min, 100 min, 105 min, 110 min, 115 min, 120 min, 125 min, 130 min, 135 min, 140 min, 145 min, 150 min, 155 min, 160 min, 165 min, 170 min, 175 min, 180 min, 185 min, 190 min, 195 min, 20° min, 205 min, 210 min, 220 min, 225 min, 230 min, 235 min, 240 min, 245 min, 250 min, 255 min, 260 min, 265 min, 270 min, 275 min, 280 min, 285 min, 290 min, 295 min, or 300 min.

In this application, the crystal Form II of potassium N-[8-(2-hydroxybenzoyl)amino]octanoate is heated to 140° C. under nitrogen protection to produce crystal Form I of potassium N-[8-(2-hydroxybenzoyl)amino]octanoate.

In this application, the crystal Form IV of potassium N-[8-(2-hydroxybenzoyl)amino]octanoate is heated to 110° C. under nitrogen protection to produce crystal Form I of potassium N-[8-(2-hydroxybenzoyl)amino]octanoate.

The present application provides a third preparation method of crystal Form I of potassium N-[8-(2-hydroxybenzoyl)amino]octanoate, wherein the crystal forms of potassium N-[8-(2-hydroxybenzoyl)amino]octanoate other than crystal Form I are lyophilized to produce crystal Form I.

In the present application, the crystal forms of potassium N-[8-(2-hydroxybenzoyl)amino]octanoate other than crystal Form I are at least one or more of crystal Form II, crystal Form III and crystal Form IV;

The present application provides a preparation method of crystal Form III of potassium N-[8-(2-hydroxybenzoyl)amino]octanoate, which comprises the following steps:

step 1: adding an organic solvent to a reaction vessel and stirring, then adding N-[8-(2-hydroxybenzoyl)amino]octanoic acid to stir evenly, adding potassium hydroxide solution dropwise, after the dropwise addition, concentrating to obtain the crude product;

step 2: adding an organic solvent to the crude product to obtain a filter cake after beating and suction filtration, preparing the filter cake into uniform particles, then placing the particles in a drying oven for drying, spreading the dried particles evenly in a low temperature environment of 2-8° C., and controlling the relative humidity to be 50% for 2 days to produce crystal Form III of potassium N-[8-(2-hydroxybenzoyl)amino]octanoate.

In the present application, the filter cake is made to pass through a 20-24 mesh sieve to obtain uniform particles.

In the present application, the drying temperature is 60-100° C., and the drying time is 30-40 h.

Preferably, the drying temperature may be 60° C., 65° C., 70° C., 75° C., 80° C., 85° C., 90° C., 95° C., or 100° C. The drying time may be 30 h, 31 h, 32 h, 33 h, 34 h, 35 h, 36 h, 37 h, 38 h, 39 h, or 40 h.

Preferably, the drying is divided into two steps, firstly drying at 60° C. for 16 h, and then drying again at 100° C. for 24 h after pressure of the system is balanced with nitrogen.

In this application, the organic solvent is isopropanol or acetone.

In the present application, the concentration of the potassium hydroxide solution is 40-90%, preferably 50%.

The concentration of the potassium hydroxide solution may be 40%, 45%, 50%, 55%, 60%, 65%, 70%, 75%, 80%, 85%, or 90%.

In this application, after adding N-[8-(2-hydroxybenzoyl)amino]octanoic acid, the temperature of the system is raised to 48° C. or above, and then potassium hydroxide solution is added dropwise, and after the dropwise addition the temperature is maintained at 48° C. or above to react for 0.5 h-2 h.

Preferably, after adding N-[8-(2-hydroxybenzoyl)amino]octanoic acid, the temperature of the system is raised to 48-52° C., and then potassium hydroxide solution is added dropwise, and after the dropwise addition the temperature is maintained at 48-52° C. to react for 1 h.

The system temperature may be 48° C., 49° C., 50° C., 51° C., 52° C., 53° C., 54° C., or 55° C.

The reaction time at a maintained temperature may be 0.5 h, 0.6 h, 0.7 h, 0.8 h, 0.9 h, 1 h, 1.1 h, 1.2 h, 1.3 h, 1.4 h, 1.5 h, 1.6 h, 1.7 h, 1.8 h, 1.9 h, or 2 h.

In this application, the molar ratio of N-[8-(2-hydroxybenzoyl)amino]octanoic acid and potassium hydroxide is 1:1.

In the present application, the beating time after adding the organic solvent to the crude product is 0.5 h-1.5 h, preferably 1 h.

The beating time after adding the organic solvent to the crude product may be 0.5 h, 0.6 h, 0.7 h, 0.8 h, 0.9 h, 1 h, 1.1 h, 1.2 h, 1.3 h, 1.4 h, 1.5 h, 1.6 h, 1.7 h, 1.8 h, 1.9 h, or 2 h.

The present application provides a preparation method of crystal Form II of potassium N-[8-(2-hydroxybenzoyl)amino]octanoate, wherein the crystal forms of potassium N-[8-(2-hydroxybenzoyl)amino]octanoate other than crystal Form II are exposed to an environment with relative humidity of 0-60% at room temperature for more than 24 h to produce crystal Form II of potassium N-[8-(2-hydroxybenzoyl)amino]octanoate.

In this application, the relative humidity is an environment with relative humidity of 20%, 30%, 40%, 50%, or 60%.

In the present application, the time for producing the crystal Form II of potassium N-[8-(2-hydroxybenzoyl)amino]octanoate may be 24 h, 25 h, 26 h, 27 h, 28 h, 29 h, 30 h, 31 h, 32 h, 33 h, 34 h, 35 h, 36 h, 37 h, 38 h, 39 h, 40 h, 41 h, 42 h, 43 h, 44 h, 45 h, 46 h, 47 h, or 48 h, etc.

In this application, the crystal forms of potassium N-[8-(2-hydroxybenzoyl)amino]octanoate other than crystal Form II are at least one or more of crystal Form I, crystal Form III and crystal Form IV.

The crystal form of potassium N-[8-(2-hydroxybenzoyl)amino]octanoate other than crystal Form II may be crystal Form I.

The crystal form of potassium N-[8-(2-hydroxybenzoyl)amino]octanoate other than crystal Form II may be crystal Form III.

The crystal form of potassium N-[8-(2-hydroxybenzoyl)amino]octanoate other than crystal Form II may be crystal Form IV.

The crystal forms of potassium N-[8-(2-hydroxybenzoyl)amino]octanoate other than crystal Form II may be crystal Form I and crystal Form III.

The crystal forms of potassium N-[8-(2-hydroxybenzoyl)amino]octanoate other than crystal Form II may be crystal Form I and crystal Form IV.

The crystal forms of potassium N-[8-(2-hydroxybenzoyl)amino]octanoate other than crystal Form II may be crystal Form III and crystal Form IV.

The crystal forms of potassium N-[8-(2-hydroxybenzoyl)amino]octanoate other than crystal Form II may be crystal Form I, crystal Form III and crystal Form IV.

The present application provides a preparation method of crystal Form IV of potassium N-[8-(2-hydroxybenzoyl)amino]octanoate, which comprises the following steps:

the crystal forms of potassium N-[8-(2-hydroxybenzoyl)amino]octanoate other than crystal Form IV are kept in an environment with higher than 80% relative humidity to form a gel-like substance;

the gel-like substance is exposed to an environment with 20-40% relative humidity at room temperature for 120 h or more to produce crystal Form IV.

In this application, the crystal forms of potassium N-[8-(2-hydroxybenzoyl)amino]octanoate other than crystal Form IV are at least one or more of crystal Form I, crystal Form II and crystal Form III.

The crystal form of potassium N-[8-(2-hydroxybenzoyl)amino]octanoate other than crystal Form IV may be crystal Form I.

The crystal form of potassium N-[8-(2-hydroxybenzoyl)amino]octanoate other than crystal Form IV may be crystal Form II.

The crystal form of potassium N-[8-(2-hydroxybenzoyl)amino]octanoate other than crystal Form IV may be crystal Form III.

The crystal forms of potassium N-[8-(2-hydroxybenzoyl)amino]octanoate other than crystal Form IV may be crystal Form I and crystal Form III.

The crystal forms of potassium N-[8-(2-hydroxybenzoyl)amino]octanoate other than crystal Form IV may be crystal Form I and crystal Form II.

The crystal forms of potassium N-[8-(2-hydroxybenzoyl)amino]octanoate other than crystal Form IV may be crystal Form III and crystal Form II.

The crystal forms of potassium N-[8-(2-hydroxybenzoyl)amino]octanoate other than crystal Form IV may be crystal Form I, crystal Form II and crystal Form III.

In the present application, the gel-like substance is exposed to an environment with 20%, 30% or 40% relative humidity, preferably 40% relative humidity.

In the present application, the crystal forms other than crystal Form IV are kept in an environment with higher than 80% relative humidity for at least two days to form a gel-like substance. The time for keeping in the above environment may be 48 h, 50 h, 55 h, 60 h, 65 h, or 72 h etc.

The time for exposing the gel-like substance to an environment with 20-40% relative humidity at room temperature to produce crystal Form IV may be 120 h, 121 h, 122 h, 123 h, 124 h, 125 h, 126 h, 127 h, 128 h, 129 h, 130 h, 131 h, 132 h, 133 h, 134 h, 135 h, 136 h, 137 h, 138 h, 139 h, or 140 h, etc.

The present application provides a pharmaceutical composition comprising a crystal polymorph of potassium N-[8-(2-hydroxybenzoyl)amino]octanoate.

The pharmaceutical composition also comprises a preventive and/or therapeutic drug, and the preventive and/or therapeutic drug may be glucagon-like peptide-1 (GLP-1 for short), insulin, PYY, human amylin, heparin, human growth hormone, interferon, monoclonal antibody, protease inhibitor, or thrombopoietin.

In the present application, the crystal polymorph of potassium N-[8-(2-hydroxybenzoyl)amino]octanoate in the pharmaceutical composition is one or more of crystal Form I, crystal Form II, crystal Form III and crystal Form IV.

The pharmaceutical composition comprises the crystal Form I of potassium N-[8-(2-hydroxybenzoyl)amino]octanoate.

The pharmaceutical composition comprises the crystal Form II of potassium N-[8-(2-hydroxybenzoyl)amino]octanoate.

The pharmaceutical composition comprises the crystal Form III of potassium N-[8-(2-hydroxybenzoyl)amino]octanoate.

The pharmaceutical composition comprises the crystal Form IV of potassium N-[8-(2-hydroxybenzoyl)amino]octanoate.

The pharmaceutical composition comprises crystal Form I and crystal Form 11 of potassium N-[8-(2-hydroxybenzoyl)amino]octanoate.

The pharmaceutical composition comprises crystal Form I and crystal Form III of potassium N-[8-(2-hydroxybenzoyl)amino]octanoate.

The pharmaceutical composition comprises crystal Form I and crystal Form IV of potassium N-[8-(2-hydroxybenzoyl)amino]octanoate.

The pharmaceutical composition comprises crystal Form II and crystal Form III of potassium N-[8-(2-hydroxybenzoyl)amino]octanoate.

The pharmaceutical composition comprises crystal Form II and crystal Form IV of potassium N-[8-(2-hydroxybenzoyl)amino]octanoate.

The pharmaceutical composition comprises crystal Form III and crystal Form IV of potassium N-[8-(2-hydroxybenzoyl)amino]octanoate.

The pharmaceutical composition comprises crystal Form I, crystal Form II and crystal Form III of potassium N-[8-(2-hydroxybenzoyl)amino]octanoate.

The pharmaceutical composition comprises crystal Form II, crystal Form III and crystal Form IV of potassium N-[8-(2-hydroxybenzoyl)amino]octanoate.

The pharmaceutical composition comprises crystal Form I, crystal Form III and crystal Form IV of potassium N-[8-(2-hydroxybenzoyl)amino]octanoate.

The pharmaceutical composition comprises crystal Form I, crystal Form II, crystal Form III and crystal Form IV of potassium N-[8-(2-hydroxybenzoyl)amino]octanoate.

In the present application, the weight ratio of crystal polymorph of potassium N-[8-(2-hydroxybenzoyl)amino]octanoate to the preventive and/or therapeutic drugs in the pharmaceutical composition may be (20-60):1.

In the present application, the weight ratio of crystal polymorph of potassium N-[8-(2-hydroxybenzoyl)amino]octanoate to the preventive and/or therapeutic drugs in the pharmaceutical composition may be 30:1.

The weight ratio of crystal polymorph of potassium N-[8-(2-hydroxybenzoyl)amino]octanoate to preventive and/or therapeutic drugs in the pharmaceutical composition may be 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, or 60:1.

The pharmaceutical composition may be in the form of a tablet.

The present application provides use of a crystal polymorph of potassium N-[8-(2-hydroxybenzoyl)amino]octanoate or a pharmaceutical composition thereof in the preparation of preventive and/or therapeutic medicaments.

The present application provides use of a crystal polymorph of potassium N-[8-(2-hydroxybenzoyl)amino]octanoate or a pharmaceutical composition thereof in the promotion of drug delivery.

The present application provides use of a crystal polymorph of potassium N-[8-(2-hydroxybenzoyl)amino]octanoate or a pharmaceutical composition thereof in the preparation of a medicament for preventing and/or treating diabetes or diabetic complications.

Preventive and/or Therapeutic Drugs

A preventive and/or therapeutic drug refers to a drug that, through use, achieves the purpose of avoiding, curing, decreasing, alleviating, altering, treating, ameliorating, improving, or affecting a pathological condition (e.g., a disease), symptoms of a disease, or susceptibility to a disease.

A preventive and/or therapeutic drug may be a protein; polypeptide; peptide; hormone; polysaccharide, mucopolysaccharide, and a specific mixture of mucopolysaccharides; carbohydrate; lipid; a small polar organic molecule (i.e. polar organic molecules with molecular weight of 500 daltons or less); other organic compounds; and certain compounds that do not pass through by themselves the gastrointestinal mucosa (only through the portion of the administered dose) and/or are susceptible to cleavage by acids and enzymatic activity in the gastrointestinal tract; or any combination of them.

Preventive and/or therapeutic drugs may be substances including, but not limited to, the following (including their synthetic, natural or recombinant sources): growth hormones, including human growth hormone (hGH), recombinant human growth hormone (rhGH), bovine growth hormone, and porcine growth hormone; growth hormone-releasing hormone; growth hormone-releasing factor (e.g., GRF analog g); interferons, including α, β and γ interferons; interleukin 1; interleukin 2; insulin, including porcine, bovine, human insulins, and human recombinant insulins, optionally with counterions including zinc, sodium, calcium and ammonium; insulin-like growth factors, including IGF-1; heparins, including unfractionated heparin, heparin analog, dermatan, chondroitin, low molecular weight heparin, very low molecular weight heparin, and ultra-low molecular weight heparin; calcitonin, including salmon, eel, porcine and human calcitonin; erythropoietin; atrial natriuretic peptide; antigen; monoclonal antibody; somatostatin; protease inhibitor; corticotropin, gonadotropin-releasing hormone; oxytocin; luteinizing hormone-releasing hormone; follitropin; glucocerebrosidase; thrombopoietin; filgrastin; prostaglandin; cyclosporine; vasopressin; sodium cromolyn (sodium cromolyn or disodium chromoglycate); vancomycin; deferoxamine (DFO); bisphosphonates, including ibandronate, alendronate, tiludronate, etidronate, clodronate, pamidronate, olpadronate, icadronate and its medicinal salts (such as sodium ibandronate); gallium salts (such as gallium nitrate, gallium nitrate nonahydrate, and gallium maltolate); acyclovir and its pharmaceutically acceptable salts (e.g., acyclovir sodium); parathyroid hormone (PTH), including fragments thereof; anti-migraine agents, such as BIBN-4096BS and other calcitonin gene-related protein antagonists; antimicrobial agents, including antibiotics (including bactericidal, lipopeptide, and cyclopeptide antibiotics that act on gram-positive bacteria, including daptomycin), antibacterial and antifungal agents; vitamins; analogs, fragments, mimetics, or polyethylene glycol (PEG)-modified derivatives of these compounds; or any combination thereof.

The preferred drugs in this application are polypeptide and protein drugs that are difficult to be absorbed in the intestinal tract after oral administration. Common drugs include insulin, monoclonal antibody, heparin, glucagon-like peptide, PYY (peptide YY), human amylin, human growth hormone, interferon, protease inhibitor, thrombopoietin, etc., including analogs, fragments, mimetics and polyethylene glycol-modified derivatives thereof.

Insulin

Insulin is a protein hormone secreted by pancreatic islet β cells in pancreas stimulated by endogenous or exogenous substances such as glucose, lactose, ribose, arginine, and glucagon. Insulin is the only hormone in the body that lowers blood sugar, while promoting synthesis of glycogen, fat, and protein. Exogenous insulin is mainly used for diabetes treatment. All crystal forms of insulin in this application include but not limited to, naturally occurring and synthetic crystal forms of insulin. Since insulin is easily degraded by oral administration, subcutaneous injection is still the main method.

PYY

PYY (peptide YY) is secreted after meals by endocrine cells in the distal gastrointestinal tract and acts on hypothalamic signaling for satiety. Recent studies have shown that, fasting and postprandial PYY levels are lower in obese subjects, which may account for their high appetite and food consumption. When administered intravenously, PYY suppresses appetite and food intake in lean and obese subjects. Other peptides from the pancreatic peptide (PP) family, such as PYY fragments (e.g., PYY[3-36]) and other PYY agonists, can also suppress appetite. However, the oral activity of PYY is essentially negligible due to its low absorption and rapid degradation in the gastrointestinal tract.

Glucagon-Like Peptide-1

Glucagon-like peptide-1 (GLP-1 for short) is a brain-gut peptide secreted by endocrine cells of ileum, and is currently mainly used as the target of type 2 diabetes drugs. Since GLP-1 may inhibit gastric emptying and reduce bowel motility, it helps to control food intake and reduce weight. However, since GLP-1 is a polypeptide, it is easy to be degraded after oral administration, and is difficult to reach the intestinal tract.

Human Amylin

Human amylin (human islet amyloid polypeptide, hIAPP) is a polypeptide hormone consisting of 37 amino acids, it is synthesized and secreted by pancreatic islet cells, and cooperates with insulin and glucagon to regulate glucose homeostasis. The physiological and pharmacological functions of hIAPP monomer are as follows: 1) affecting the secretion of insulin and glucagon; 2) delaying gastric emptying and reducing postprandial blood glucose; 3) elevating renin and angiotensin II to regulate kidney growth; 4) increasing aldosterone, and reducing blood calcium; 5) regulating bone density; 6) relaxing blood vessels, regulating hemodynamics; 7) regulating immune effects. hIAPP monomer may induce regulatory T cell differentiation, thereby regulating the inflammatory response and the secretion of immune factors. hIAPP has potential application prospects in prevention and treatment of obesity, diabetes, autoimmunity, osteoporosis and other diseases.

Pharmaceutical Composition

In addition to the PNAC and preventive and/or therapeutic drugs according to the present application, the pharmaceutical composition may further comprise pharmaceutically acceptable excipient(s), which may be a non-toxic filler, stabilizer, diluent, carrier, solvent, or other preparation excipients. For example, diluents, excipients, such as microcrystalline cellulose, mannitol, etc.; fillers, such as starch, sucrose, etc.; binders, such as starch, cellulose derivatives, alginates, gelatin, and/or polyethylene pyrrolidone; disintegrants, such as calcium carbonate and/or sodium bicarbonate; absorption enhancers, such as quaternary ammonium compounds; surfactants, such as hexadecanol; carriers, solvents, such as water, physiological saline, kaolin, bentonite, etc.; lubricants such as talc, calcium/magnesium stearate, polyethylene glycol, etc. In addition, the pharmaceutical composition according to the present application is preferably an injection.

The pharmaceutical composition is preferably in solid form, and it may be formulated into solid dosage form. Solid dosage form may be capsule, tablet or granule, such as powder or sachet. Powder may be sachet that is mixed with a liquid for administration. Solid dosage form may also be topical delivery system such as ointment, cream or semisolid. Contemplated solid dosage form may include sustained or controlled release system. Preferred solid dosage forms are those for oral administration.

The powder may be packaged into capsules or compressed into tablets, used in powder form, or incorporated into ointments, creams or semisolids. Methods for forming solid dosage forms are well known in the art.

The PNAC of this application may be used as a delivery agent in the pharmaceutical composition.

The amount of delivery agent in a solid dosage form is a delivery effective amount, and may be determined for any particular compound or biologically or chemically active agent by methods well known to those skilled in the art.

Following administration, an active agent in the unit dosage form is absorbed into the circulation. The bioavailability of an active agent is readily assessed by measuring known pharmacological activities in plasma (e.g., increased clotting time by heparin or decreased circulating levels of calcium by calcitonin). Alternatively, circulating levels of the active agent itself may be measured directly.

Delivery System

The amount of preventive and/or therapeutic drug (which may be referred to as an active agent) used in the pharmaceutical composition according to the present application is an effective amount to achieve the purpose of the active agent for the target indication. The amount of active agent in the composition will generally be a pharmacologically, biologically, therapeutically or chemically effective amount. However, this amount may be lower than when the composition is used in a unit dosage form, since a unit dosage form may contain multiple delivery agent compound/active agent compositions, or may contain divided pharmacologically, biologically, therapeutically or actively effective amounts. The total effective amount may be administered in cumulative units containing in total the effective amount of the active agent.

The total amount of active agent used may be determined by methods known to those skilled in the art. However, since the composition according to the present application may deliver the active agent more effectively than other compositions or compositions containing the active agent alone, compared with that used in the existing unit dosage or delivery system, lower amount of biological or chemical active agent may be used in a subject while still achieving the same plasma levels and/or therapeutic effect.

The delivery agents disclosed herein facilitate delivery of biologically and chemically active agents, particularly the deliveries by oral, sublingual, buccal, intraduodenal, intracolonic, rectal, vaginal, mucosal, pulmonary, intranasal, and ocular systems.

The compound and composition according to the present application are used to administer biologically or chemically active agents to any animal, including but not limited to: bird, such as chicken; mammal, such as rodent, cattle, pig, dog, cat, and primate especially humans; and insects.

These compounds and compositions are particularly advantageous for delivery of chemically or biologically active agents that may otherwise be destroyed or have reduced activity before reaching the target area (i.e., the area where the active agent of the delivery composition is released) and in the animals to which they are administered. In particular, the compounds and compositions according to the present application are useful for oral administration of active agents, especially those that are not routinely delivered orally, or those that require enhanced delivery.

A composition comprising said compound and active agent has the utility of delivering the active agent to the chosen biological system and increasing or enhancing the bioavailability of the active agent as compared with delivery of the active agent without using a delivery agent. Delivery may be improved by delivering more active agents over a period of time, or by delivering the active agent over a specific period of time (such as faster action or delayed delivery) or over a period of time (such as sustained delivery).

EXAMPLES

The experimental methods used in the following examples are conventional methods unless otherwise required.

The materials, reagents, etc. used in the following examples are commercially available unless otherwise specified.

Example 1

Preparation of N-[8-(2-hydroxybenzoyl)amino]octanoic acid NAC was done with reference to the method in Example 1 of International Patent Application WO2008/028859.

Preparation of PNAC Crystal Form I

Isopropanol (22070.0 ml, 4.0 vol) was added to a 50 L reactor to start stirring, and NAC (5518 g, 1.0 eq) was added. The system was heated to 50° C., and the prepared 50% potassium hydroxide solution (1304.0 g, 1.0 eq) was added dropwise to the system. After the dropwise addition, the system turned into a clear and transparent yellow solution, and the reaction was kept at 50° C. for 1 h. The reaction solution was concentrated in batches at 40° C. to obtain a crude product with a pale orange color.

The batches of crude product were pooled to add in isopropanol (19310.0 ml, 3.5 vol) for beating for 1 h. The system was subjected to suction filtration, and the resulting filter cake was rinsed with isopropanol (2760.0 ml, 0.5 vol). Then the filter cake was transferred to a vacuum drying oven, the pressure of the drying system was balanced with nitrogen, drying at 60° C. for 16 h, and then transferring to a vacuum drying oven and drying at 100° C. for 24 h. After drying, 4.52 kg of product in total was obtained with a yield of 72.8%, presenting as off-white powdery solids.

Figure 2A:
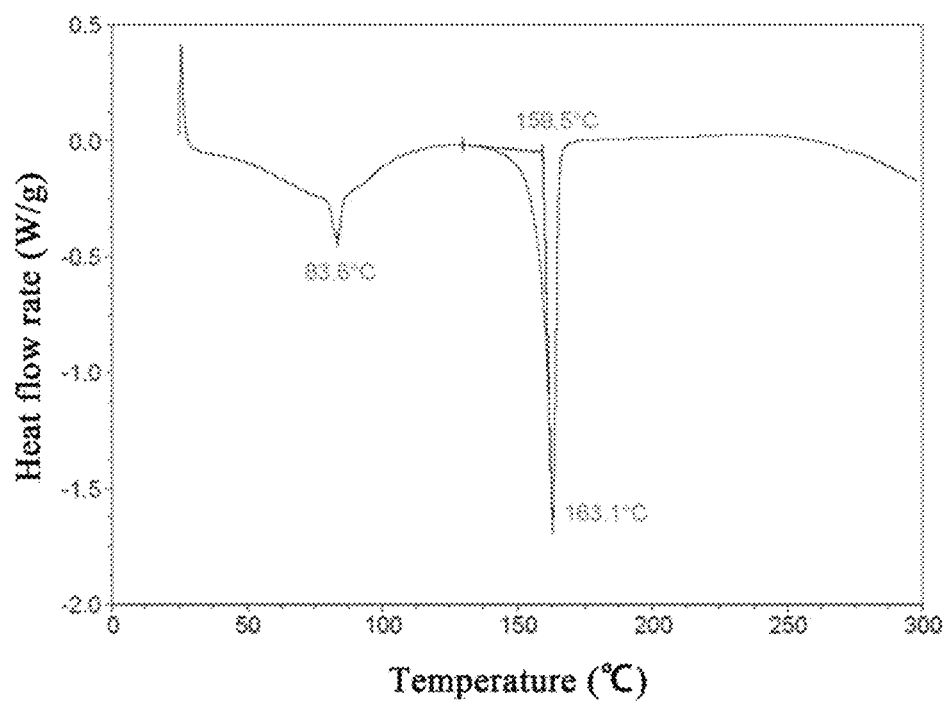
FIG. 2a is a DSC plot of the crystal Form I of PNAC prepared in Example 1.
Figure 2B:
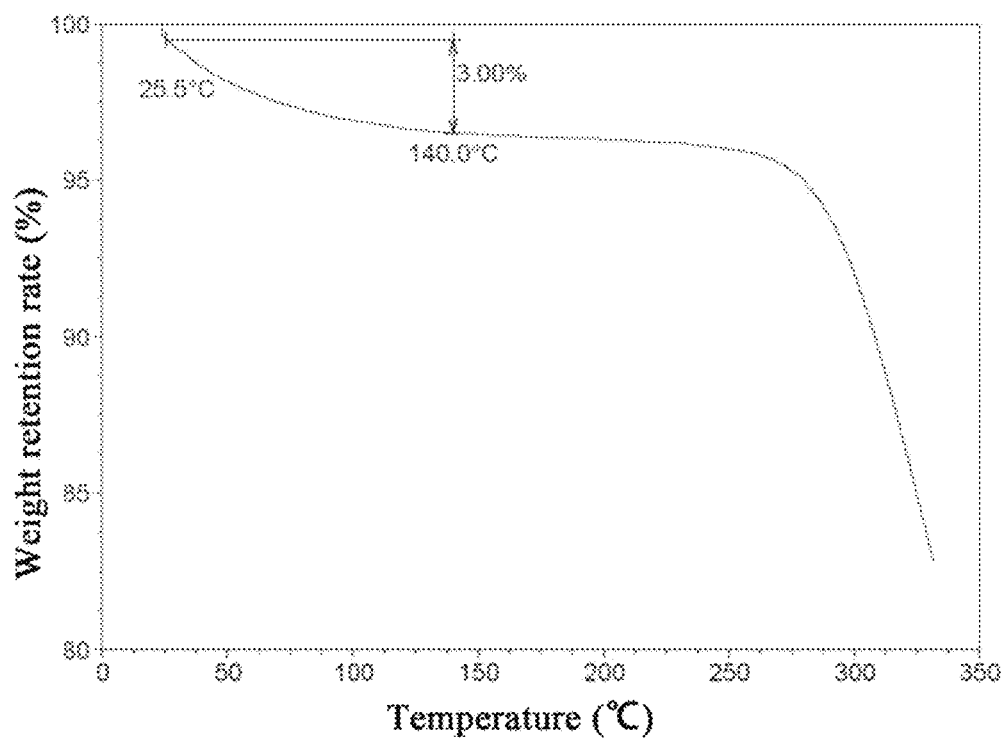
FIG. 2b is a TGA plot of the crystal Form I of PNAC prepared in Example 1.

After determination, the product is crystal Form I, the XRPD and TGA/DSC of crystal Form I are shown in FIGS. 1-2b respectively, PNAC is crystal Form I, and the characteristic XRPD peaks of crystal Form I (characterized by °2θ) are as follows in Table 1:

TABLE 1

The characteristic XRPD peaks of the crystal Form I (characterized by °2θ)

| No. | Pos. [°2θ] | Height [cts] | FWHM Left [°2θ] | d-spacing [Å] | Rel. Int. [%] |
| --- | --- | --- | --- | --- | --- |
| 1 | 7.83 | 3729.85 | 0.1338 | 11.30 | 100.00 |
| 2 | 26.64 | 1598.39 | 0.2676 | 3.35 | 42.85 |
| 3 | 18.89 | 1179.42 | 0.6022 | 4.70 | 31.62 |
| 4 | 5.24 | 719.71 | 0.1673 | 16.87 | 19.30 |
| 5 | 21.59 | 593.27 | 0.4015 | 4.12 | 15.91 |
| 6 | 13.02 | 364.06 | 0.2007 | 6.80 | 9.76 |
| 7 | 24.29 | 323.05 | 0.4015 | 3.66 | 8.66 |
| 8 | 6.61 | 235.01 | 0.4015 | 13.37 | 6.30 |
| 9 | 10.43 | 158.49 | 0.2676 | 8.48 | 4.25 |
| 10 | 31.63 | 145.22 | 0.4015 | 2.83 | 3.89 |
| 11 | 37.00 | 106.05 | 0.5353 | 2.43 | 2.84 |

The DSC pattern (FIG. 2a) shows that, the crystal Form I begins to have a melting endothermic peak at 159.5° C., with a peak of 163.1° C.; the combination of the DSC (FIG. 2a) and TGA (FIG. 2b) patterns shows that the crystal Form I is anhydrous.

Example 2

Preparation of PNAC Crystal Form II

The PNAC crystal Form I prepared in Example 1 was exposed to an environment of 60% relative humidity at room temperature, and the storage time was longer than 24 h to obtain a product.

Figure 4A:
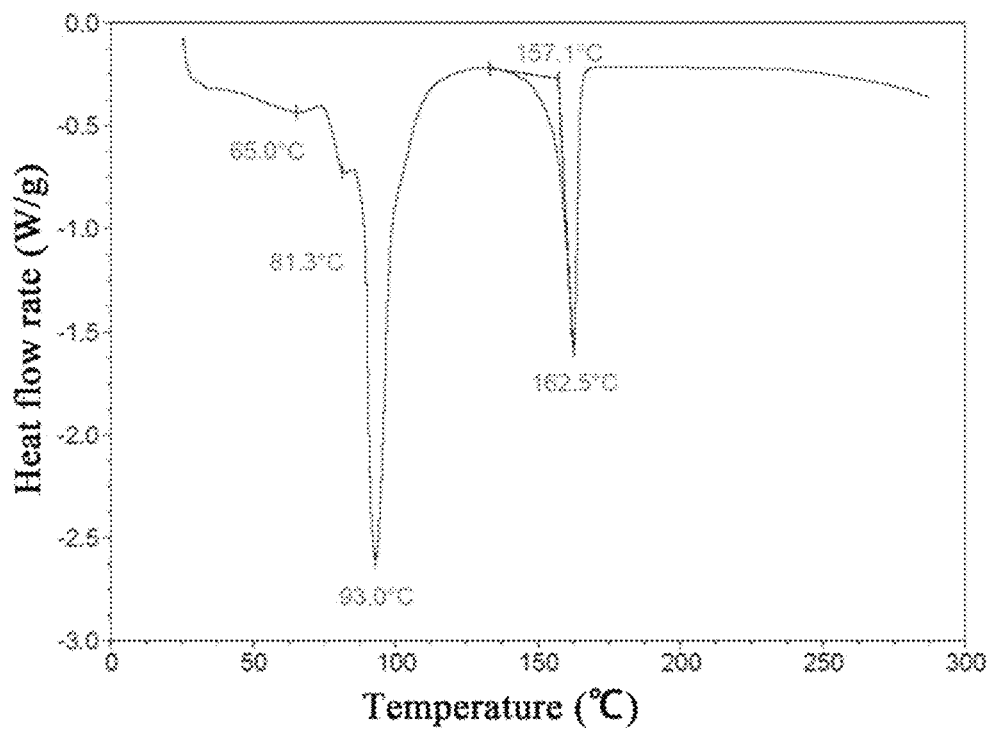
FIG. 4a is a DSC plot of the crystal Form II of PNAC prepared in Example 2.
Figure 4B:
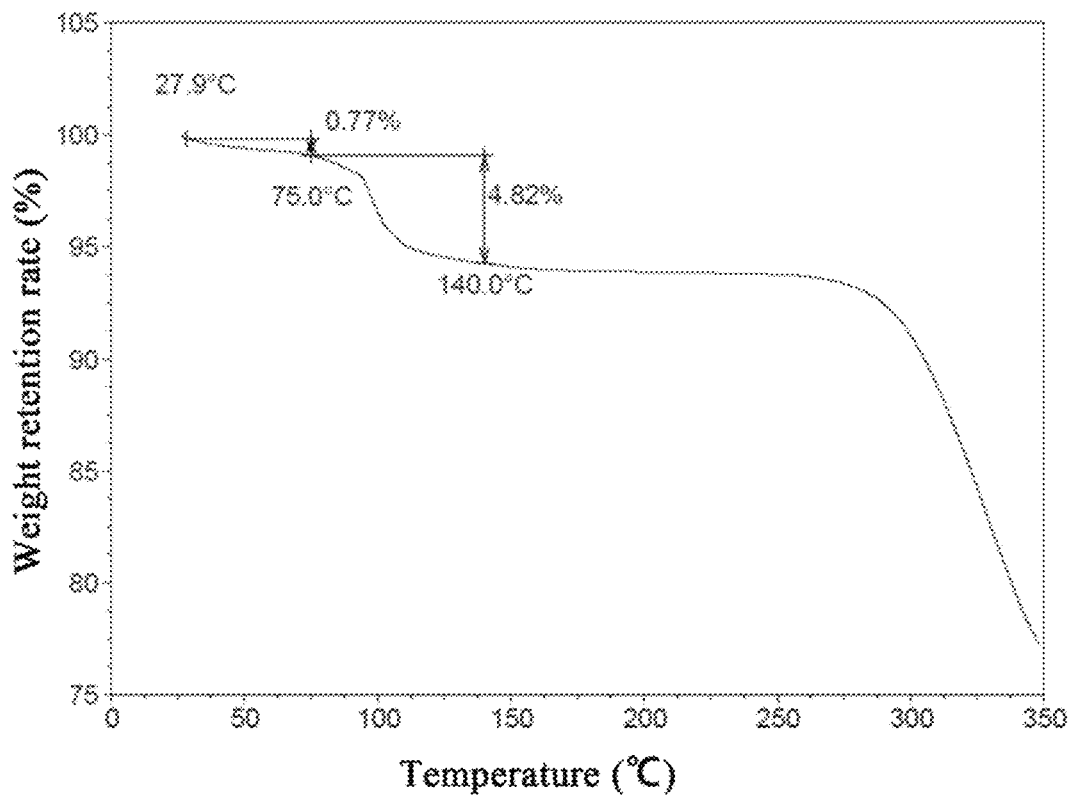
FIG. 4b is a TGA plot of the crystal Form II of PNAC prepared in Example 2.

After determination, the product is crystal Form II, and the XRPD and TGA/DSC patterns of the product are shown in FIG. 3-4b respectively, wherein the characteristic XRPD peaks of crystal Form II (characterized by °2θ) are as follows in Table 2:

TABLE 2

The characteristic XRPD peaks of the crystal Form II (characterized by °2θ)

| No. | Pos. [°2θ] | Height [cts] | FWHM Left [°2θ] | d-spacing [Å] | Rel. Int. [%] |
| --- | --- | --- | --- | --- | --- |
| 1 | 24.76 | 3034.00 | 0.1535 | 3.60 | 100.00 |
| 2 | 6.73 | 2529.55 | 0.1279 | 13.13 | 83.37 |
| 3 | 20.26 | 1754.20 | 0.1535 | 4.38 | 57.82 |
| 4 | 14.68 | 1173.61 | 0.1279 | 6.03 | 38.68 |
| 5 | 25.55 | 1158.21 | 0.1279 | 3.49 | 38.17 |
| 6 | 13.41 | 1037.32 | 0.1279 | 6.60 | 34.19 |
| 7 | 26.66 | 968.20 | 0.1279 | 3.34 | 31.91 |
| 8 | 21.08 | 819.28 | 0.1279 | 4.21 | 27.00 |
| 9 | 25.79 | 793.26 | 0.1023 | 3.45 | 26.15 |
| 10 | 28.47 | 661.49 | 0.1279 | 3.14 | 21.80 |
| 11 | 12.07 | 618.23 | 0.1023 | 7.33 | 20.38 |
| 12 | 15.38 | 484.74 | 0.1279 | 5.76 | 15.98 |
| 13 | 23.38 | 483.11 | 0.1791 | 3.81 | 15.92 |
| 14 | 29.48 | 479.12 | 0.1535 | 3.03 | 15.79 |
| 15 | 22.55 | 426.46 | 0.1279 | 3.94 | 14.06 |
| 16 | 27.79 | 418.36 | 0.1791 | 3.21 | 13.79 |

TABLE 2-continued

The characteristic XRPD peaks of the crystal Form II (characterized by °2θ)

| No. | Pos. [°2θ] | Height [cts] | FWHM Left [°2θ] | d-spacing [Å] | Rel. Int. [%] |
|---|---|---|---|---|---|
| 17 | 8.91 | 312.69 | 0.1279 | 9.93 | 10.31 |
| 18 | 33.09 | 291.63 | 0.1279 | 2.71 | 9.61 |
| 19 | 31.97 | 259.96 | 0.1791 | 2.80 | 8.57 |
| 20 | 30.10 | 201.77 | 0.3070 | 2.97 | 6.65 |
| 21 | 17.84 | 197.74 | 0.1535 | 4.97 | 6.52 |
| 22 | 32.44 | 192.70 | 0.1535 | 2.76 | 6.35 |
| 23 | 31.12 | 174.51 | 0.1535 | 2.87 | 5.75 |
| 24 | 22.06 | 169.20 | 0.2047 | 4.03 | 5.58 |
| 25 | 38.44 | 143.25 | 0.1791 | 2.34 | 4.72 |
| 26 | 37.16 | 132.56 | 0.2558 | 2.42 | 4.37 |
| 27 | 35.73 | 119.01 | 0.3070 | 2.51 | 3.92 |
| 28 | 35.16 | 100.94 | 0.2047 | 2.55 | 3.33 |
| 29 | 36.30 | 95.07 | 0.3070 | 2.47 | 3.13 |
| 30 | 34.51 | 71.18 | 0.3070 | 2.60 | 2.35 |

The DSC pattern (FIG. 4a) shows that, the crystal Form II begins to have a melting endothermic peak at 157.1° C., with a peak of 162.5° C.; the combination of the DSC (FIG. 4a) and TGA (FIG. 4b) patterns shows that the crystal Form II is a ⅓ hydrate.

Example 3

Preparation of N-[8-(2-hydroxybenzoyl)amino]octanoic acid NAC was done with reference to the method in Example 1 of international patent application WO2008/028859

Preparation of PNAC Crystal Form III

Isopropanol (22070.0 ml, 4.0 vol) was added to a 50 L reactor to start stirring, and NAC (5518 g, 1.0 eq) was added. The system was heated to 50° C., and the prepared 50% potassium hydroxide solution (1304.0 g, 1.0 eq) was added dropwise to the system. After the dropwise addition, the system turned into a clear and transparent yellow solution, and the reaction was kept at 50° C. for 1 h. The reaction solution was concentrated in batches at 40° C. to obtain a crude product with a pale orange color.

The batches of crude product were pooled to add in isopropanol (19310.0 ml, 3.5 vol) for beating for 1 h. The system was subjected to suction filtration to obtain a filter cake, and the filter cake was made to pass through a 24-mesh sieve to prepare uniform particles, then transferring the particles to a vacuum drying oven for drying; the pressure of the drying system was balanced with nitrogen, drying at 60° C. for 16 h, and transferring to a vacuum drying oven again for drying for 24 h under the condition of 100° C. to get dried particles; and the dried particles were evenly spread in a 5° C. low temperature environment with a controlled relative humidity of 50% to keep for 2 days to obtain the product.

Figure 6A:
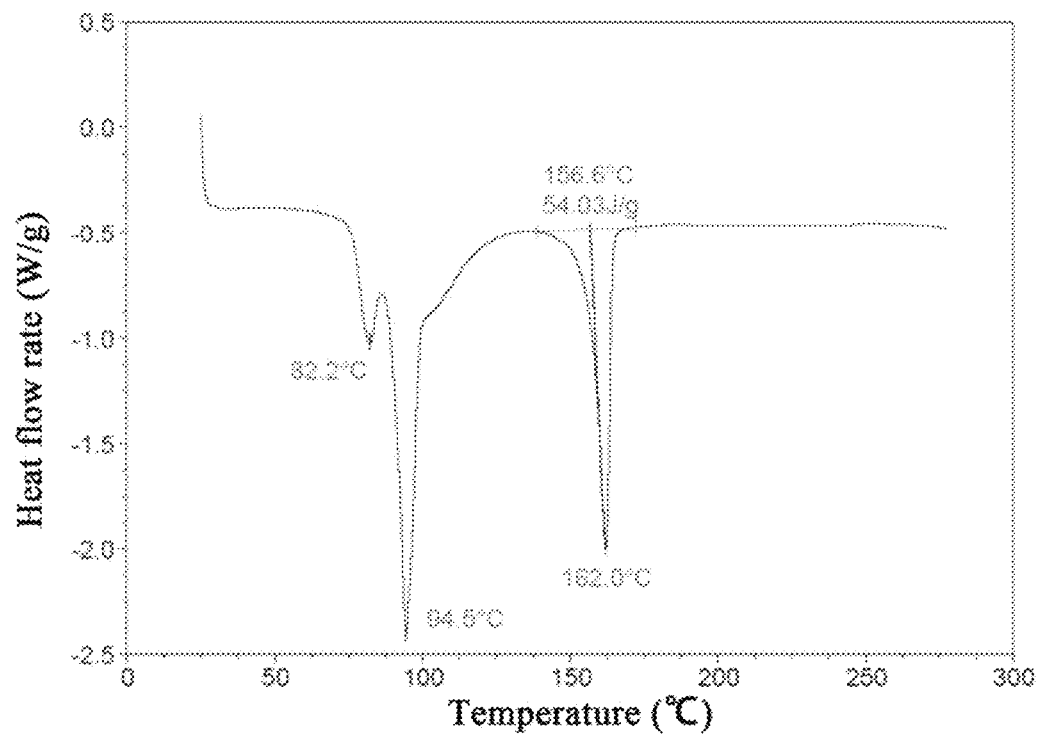
FIG. 6a is a DSC plot of the crystal Form III of PNAC prepared in Example 3.
Figure 6B:
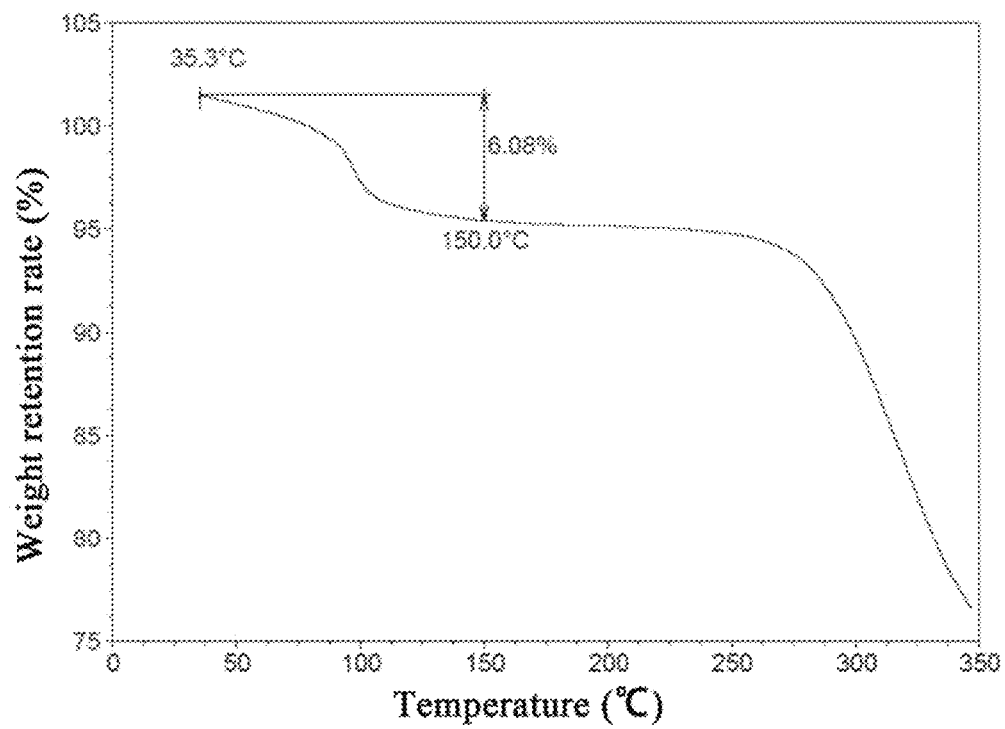
FIG. 6b is a TGA plot of the crystal Form III of PNAC prepared in Example 3.

After determination, the product is crystal Form III, and the XRPD and TGA/DSC patterns of crystal Form III are shown in FIG. 5-6b respectively, wherein the characteristic XRPD peaks of crystal Form III (characterized by °2θ) are as follows in Table 3:

TABLE 3

The characteristic XRPD peaks of the crystal Form III (characterized by °2θ)

| No. | Pos. [°2θ] | Height [cts] | FWHM Left [°2θ] | d-spacing [Å] | Rel. Int. [%] |
|---|---|---|---|---|---|
| 1 | 9.06 | 4411.48 | 0.1791 | 9.76 | 100.00 |
| 2 | 23.30 | 1866.06 | 0.1535 | 3.82 | 42.30 |
| 3 | 21.44 | 1304.70 | 0.1023 | 4.14 | 29.58 |
| 4 | 24.75 | 1057.87 | 0.1279 | 3.60 | 23.98 |
| 5 | 6.03 | 1035.59 | 0.1023 | 14.65 | 23.48 |
| 6 | 21.20 | 985.80 | 0.1023 | 4.19 | 22.35 |
| 7 | 17.06 | 889.06 | 0.1023 | 5.20 | 20.15 |
| 8 | 21.75 | 592.68 | 0.1023 | 4.09 | 13.43 |
| 9 | 29.52 | 579.93 | 0.1535 | 3.03 | 13.15 |
| 10 | 22.15 | 572.66 | 0.2047 | 4.01 | 12.98 |
| 11 | 15.11 | 555.51 | 0.1279 | 5.86 | 12.59 |
| 12 | 28.47 | 547.35 | 0.1791 | 3.14 | 12.41 |
| 13 | 22.54 | 529.25 | 0.1279 | 3.94 | 12.00 |
| 14 | 30.71 | 440.99 | 0.1023 | 2.91 | 10.00 |
| 15 | 17.91 | 410.56 | 0.1023 | 4.95 | 9.31 |
| 16 | 15.64 | 347.69 | 0.1279 | 5.67 | 7.88 |
| 17 | 26.49 | 308.77 | 0.1535 | 3.37 | 7.00 |
| 18 | 25.58 | 284.86 | 0.1535 | 3.48 | 6.46 |
| 19 | 23.98 | 284.58 | 0.1279 | 3.71 | 6.45 |
| 20 | 24.23 | 282.45 | 0.1535 | 3.67 | 6.40 |
| 21 | 11.17 | 251.72 | 0.1023 | 7.92 | 5.71 |
| 22 | 14.74 | 230.59 | 0.1023 | 6.01 | 5.23 |
| 23 | 12.05 | 212.59 | 0.1023 | 7.34 | 4.82 |
| 24 | 19.42 | 205.28 | 0.1279 | 4.57 | 4.65 |
| 25 | 33.65 | 184.35 | 0.2047 | 2.66 | 4.18 |
| 26 | 31.74 | 162.19 | 0.1535 | 2.82 | 3.68 |
| 27 | 36.75 | 110.15 | 0.2047 | 2.45 | 2.50 |
| 28 | 35.34 | 102.63 | 0.2047 | 2.54 | 2.33 |

The DSC pattern (FIG. 6a) shows that, the crystal Form III begins to have a melting endothermic peak at 156.6° C., with peak of 162.0° C., the combination of the DSC (FIG. 6a) and TGA (FIG. 6b) patterns shows that the crystal Form III is a ½ hydrate.

Example 4

Preparation of PNAC Crystal Form IV

The PNAC crystal Form I prepared in Example 1 was exposed to an environment of 80% relative humidity at room temperature, keeping for 3 days to form a gel-like substance, and the gel-like substance was exposed to an environment of 40% relative humidity, keeping for 5 days to form the product.

Figure 8A:
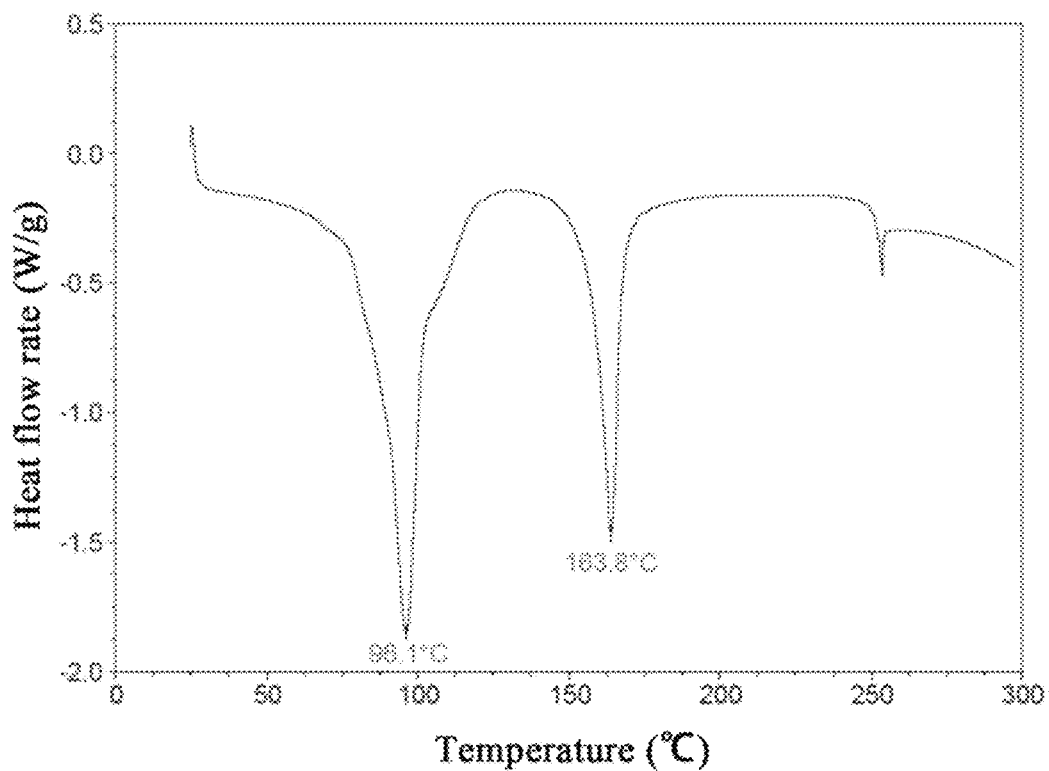
FIG. 8a is a DSC plot of the crystal Form IV of PNAC prepared in Example 4.
Figure 8B:
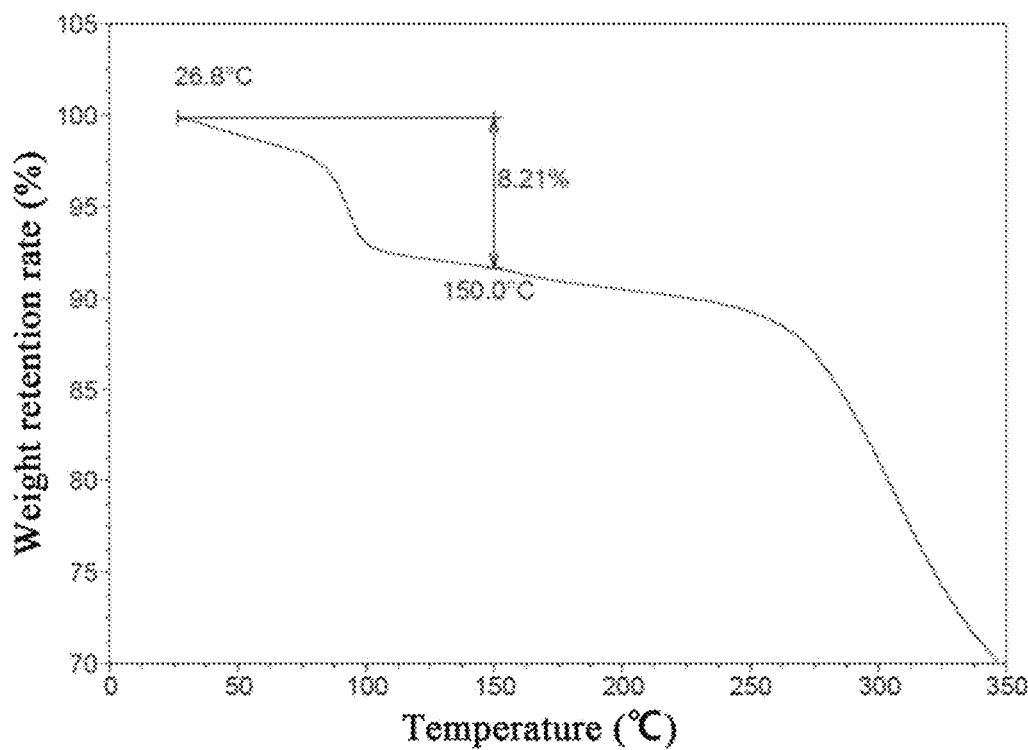
FIG. 8b is a TGA plot of the crystal Form IV of PNAC prepared in Example 4.

After determination, the product is crystal Form IV, and the XRPD and TGA/DSC patterns of crystal Form IV are shown as FIGS. 7-8b, respectively, and the characteristic XRPD peaks of crystal Form IV (characterized by °2θ) are as follows in Table 4:

TABLE 4

The characteristic XRPD peaks of the crystal Form IV (characterized by °2θ)

| No. | Pos. [°2θ] | Height [cts] | FWHM Left [°2θ] | d-spacing [Å] | Rel. Int. [%] |
|---|---|---|---|---|---|
| 1 | 16.25 | 3807.75 | 0.1023 | 5.45 | 100 |
| 2 | 6.8 | 1777.44 | 0.1535 | 13 | 46.68 |
| 3 | 22.08 | 1009.85 | 0.1279 | 4.03 | 26.52 |
| 4 | 13.16 | 993.01 | 0.1023 | 6.73 | 26.08 |
| 5 | 19.39 | 952.71 | 0.1535 | 4.58 | 25.02 |
| 6 | 18.35 | 797.81 | 0.1023 | 4.84 | 20.95 |
| 7 | 9.68 | 766.82 | 0.1023 | 9.14 | 20.14 |
| 8 | 15.92 | 759.06 | 0.1279 | 5.57 | 19.93 |

TABLE 4-continued

The characteristic XRPD peaks of the crystal Form IV (characterized by °2θ)

| No. | Pos. [°2θ] | Height [cts] | FWHM Left [°2θ] | d-spacing [Å] | Rel. Int. [%] |
|---|---|---|---|---|---|
| 9 | 11.71 | 616.63 | 0.1279 | 7.56 | 16.19 |
| 10 | 29.91 | 573.03 | 0.1535 | 2.99 | 15.05 |
| 11 | 23.04 | 570.17 | 0.1535 | 3.86 | 14.97 |
| 12 | 16.56 | 536.27 | 0.1535 | 5.35 | 14.08 |
| 13 | 23.5 | 350.18 | 0.1279 | 3.79 | 9.2 |
| 14 | 27.31 | 311.67 | 0.1791 | 3.27 | 8.19 |
| 15 | 19.74 | 249.5 | 0.1535 | 4.5 | 6.55 |
| 16 | 34.34 | 199.39 | 0.307 | 2.61 | 5.24 |
| 17 | 18.82 | 195.68 | 0.1023 | 4.71 | 5.14 |
| 18 | 24.76 | 192.59 | 0.1279 | 3.6 | 5.06 |
| 19 | 17.01 | 163.32 | 0.1535 | 5.21 | 4.29 |
| 20 | 28.02 | 156.42 | 0.2047 | 3.18 | 4.11 |
| 21 | 26.48 | 144.96 | 0.1535 | 3.37 | 3.81 |
| 22 | 30.58 | 134.01 | 0.15.35 | 2.92 | 3.52 |
| 23 | 25.23 | 130.59 | 0.1535 | 3.53 | 3.43 |
| 24 | 29.29 | 125.18 | 0.15.35 | 3.05 | 3.29 |
| 25 | 37.18 | 124.21 | 0.307 | 2.42 | 3.26 |
| 26 | 26.03 | 116.9 | 0.2047 | 3.42 | 3.07 |
| 27 | 20.94 | 113.62 | 0.1535 | 4.24 | 2.98 |
| 28 | 33.43 | 66.95 | 0.307 | 2.68 | 1.76 |
| 29 | 36 | 67.05 | 0.2047 | 2.5 | 1.76 |

The DSC pattern (FIG. 8a) shows that, the melting endothermic peak of the crystal Form IV is 163.8° C., the combination of DSC (FIG. 8a) and TGA (FIG. 8b) patterns shows that crystal Form IV is a monohydrate.

Experimental Examples

SNAC:

SNAC in Rybelsus® tablets (developed by Novo Nordisk, Danish pharmaceutical company) was characterized, and found to be identical to crystal Form I in patent WO2005107462. Therefore, the SNACs herein were prepared by referring to the preparation method of SNAC crystal Form I in Example 1 of patent WO2005107462. All the SNACs in the following examples were prepared by this method.

Crystal Form I (PNAC-I) was prepared in Example 1.
Crystal Form II (PNAC-II) was prepared in Example 2.
Crystal Form III (PNAC-III) was prepared in Example 3.
Crystal Form IV (PNAC-IV) was prepared in Example 4.

Experimental Example 1: Experiments on Solution Stability of Different Crystal Forms of PNAC in Aqueous Solution The samples of PNAC crystal forms I to IV prepared in the preceding Examples and the SNAC crystal Form I samples prepared in the preceding Examples were respectively dissolved in purified water, placing under two conditions of 4° C. and room temperature (RT) respectively, and the changes of the solutions were observed. The stability differences between different salt forms and different crystal forms in aqueous solution under the condition of high concentration (500 mg/mL) were compared, and the results are shown in Table 5 (there is no difference in the dissolution and solution storage process of the samples of PNAC crystal forms I-IV).

TABLE 5

Solubility of different crystal forms of PNAC under different dissolution conditions

| Storage time/h | SNAC | | PNAC I | | PNAC II | | PNAC III | | PNAC IV | |
|---|---|---|---|---|---|---|---|---|---|---|
| | 4° C. | RT | 4° C. | RT | 4° C. | RT | 4° C. | RT | 4° C. | RT |
| 0.0 | When it was dissolved, there were many bubbles in the light brown solution, and the liquid had a certain viscosity. | | When it was dissolved, there were few bubbles in the light yellow solution, and the liquid had a certain viscosity. | | When it was dissolved, there were few bubbles in the light yellow solution, and the liquid had a certain viscosity. | | When it was dissolved, there were few bubbles in the light yellow solution, and the liquid had a certain viscosity. | | When it was dissolved, there were few bubbles in the light yellow solution, and the liquid had a certain viscosity. | |
| 0.5 | There were flocs in the solution. | There was no change in the solution. | There was no change in the solution. | | There was no change in the solution. | | There was no change in the solution. | | There was no change in the solution. | |
| 1.0 | The flocs in the solution increased, the solution became turbid, and the fluidity decreased. | There were flocs in the solution, and the transparency decreased. | There were few filamentous flocs in the bottom of the solution and no other changes. | There was no change in the solution. | There were few filamentous flocs in the bottom of the solution and no other changes. | There was no change in the solution. | There were few filamentous flocs in the bottom of the solution and no other changes. | There was no change in the solution. | There were few filamentous flocs in the bottom of the solution and noother changes. | There was no change in the solution. |
| 2.0 | The fluidity was further reduced and the solution was pasty; white large particles were precipitated. | The flocs in the solution increased, andthe solution became turbid. | There were a few more filamentous flocs in the bottom of the solution and no other changes. | There were few flocs in the solution and no other changes. | There were a few more filamentous flocs in the bottom of the solution and no other changes. | There were few flocs in the solution and no other changes. | There were a few more filamentous flocs in the bottom of the solution and no other changes. | There were few flocs in the solution and no other changes. | There were a few more filamentous flocs in the bottom of the solution and no other changes. | There were few flocs inthe solution and no other changes. |

It can be seen from Table 5 that, after dissolving SNAC at 4° C., flocs began to appear in the solution at 0.5 h, the fluidity of the solution gradually deteriorated over time, and large white particles were precipitated in the solution at 2 h; when the temperature was increased to room temperature, flocs began to appear in the SNAC solution after keeping for 1 h, and after 2 h the flocs would increase and the solution became turbid. However, after keeping the PNAC I-IV solution prepared in this application at 4° C. for 1 h, a small amount of filamentous flocs appeared at the bottom, and the state of the solution did not change much until 2 h; after keeping at room temperature for 2 h only a small amount of flocs appeared in the solution. This shows that under the same conditions, the stability of the PNAC I-IV solution of the present application is better than that of SNAC under the condition of high concentration (500 mg/mL).

Experimental Example 2: The Effects of Different Crystal Forms of PNAC on the Bioavailability of GLP-1 Peptide in Beagle Dogs For the preparation method of GLP-1 peptide M4 (M4 for short), please refer to PCT application WO2019201328.

For the preparation method of the combined oral tablet, refer to the preparation method in Example 1 of PCT application WO2012080471. The delivery agents (SNAC, PNAC-I, and PNAC-II) were combined with M4 respectively. The combined oral tablet prepared by combining SNAC and M4 was SNAC+M4. The combined oral tablet prepared by combining PNAC-I and M4 was PNAC-I+M4. The combined oral tablet prepared by combining PNAC-II and M4 was PNAC-II+M4.

In the combined oral tablet: there were 10 mg of M4, and 100 mg of delivery agent.

Prescription for intravenous injection of M4: M4 was dissolved in 8 mM phosphate buffer (pH 7.2) to give a final M4 concentration of 1 mg/mL.

Twenty-eight male beagle dogs with body weights of 9-12 kg were selected, and divided into 4 groups. The first group received a single intravenous injection of M4 (0.05 mg/kg, N=4), and the second group took a single oral dose of SNAC+M4 (1 tablet, N=8), the third group took a single oral dose of PNAC-I+M4 (1 tablet, N=8), the fourth group took a single oral dose of PNAC-II+M4 (1 tablet, N=8), and then the effects of different PNAC crystal forms on the bioavailability of M4 in beagle dogs were compared.

Figure 9:
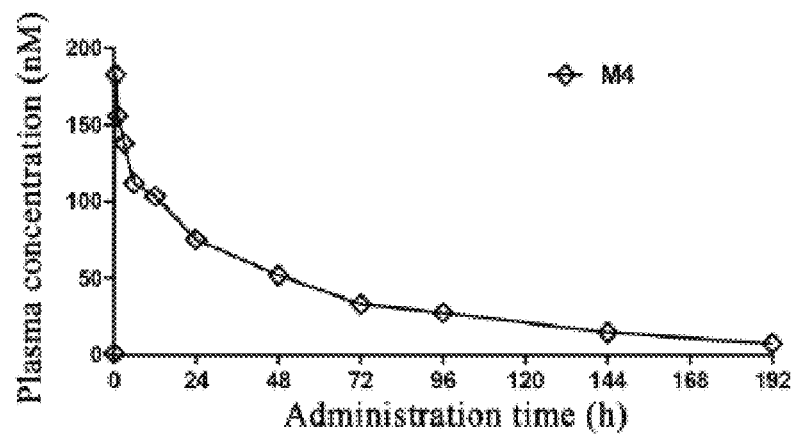
FIG. 9 is a trend plot of plasma concentration vs. administration time in the intravenous administration group.
Figure 10:
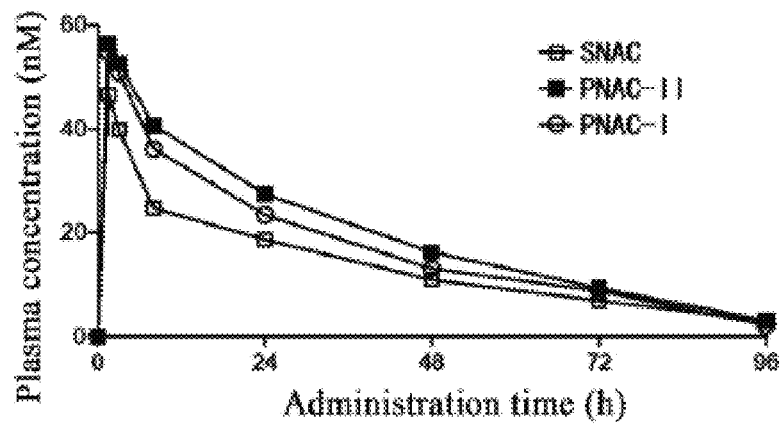
FIG. 10 is a trend plot of plasma concentration vs. administration time in each of the oral administration groups.

The beagle dogs in the oral administration groups were fasted with free access to water in the previous night. On the same day, the tablet was taken with 10 ml of water (quantitative), and 4 h later food intake was resumed for the dogs. Then the plasma concentrations at different time points were measured according to the plasma sampling scheme in Table 6, and the exposure $AUC_{last}$ in animals was calculated. The specific results are shown in Tables 7-9 and FIGS. 9-10.

TABLE 6

The plasma sampling scheme

| Groups | Time points of plasma sampling |
|---|---|
| M4 intravenous injection group | predose, 0.5, 1, 3, 6, 12, 24, 48, 72, 96, 144 and 192 h after the dosing |
| Oral administration group | predose, 1.5, 3, 8, 24, 48, 72, 96 h after the dosing |

Note:
At least 500 μl plasma, at each time point

TABLE 7

Summary of plasma concentrations at different time points in the intravenous injection group

| | Plasma concentration (nM)-Administration time (h) | | | | | | | | | | |
|---|---|---|---|---|---|---|---|---|---|---|---|
| Group | 0 h | 0.5 h | 1 h | 3 h | 6 h | 12 h | 24 h | 48 h | 72 h | 96 h | 144 h | 192 h |
| M4 | 0.91 | 182.54 | 155.90 | 137.96 | 111.83 | 103.66 | 75.20 | 52.06 | 33.01 | 27.50 | 14.67 | 7.55 |

TABLE 8

Summary of the plasma concentrations at different time points in each oral administration group

| | Plasma concentration (nM)-Administration time (h) | | | | | | | |
|---|---|---|---|---|---|---|---|---|
| Groups | 0 h | 1.5 h | 3 h | 8 h | 24 h | 48 h | 72 h | 96 h |
| SNAC | 0 | 46.72 | 39.99 | 24.75 | 18.74 | 10.98 | 6.94 | 3.11 |
| PNAC-I | 0 | 54.86 | 50.93 | 36.21 | 23.54 | 13.15 | 8.81 | 2.19 |
| PNAC-II | 0 | 56.46 | 52.78 | 40.74 | 27.53 | 16.31 | 9.37 | 3.12 |

TABLE 9

Summary of drug exposure ($AUC_{last}$) comparison in animals of each group

| Groups | Dosage of administration | Route of administration | $AUC_{last}$ (nM*h) |
|---|---|---|---|
| 1 | M4 | Intravenous injection | 7338.09 |
| 2 | SNAC | Oral administration | 1302.12 |
| 3 | PNAC-I | | 1652.14 |
| 4 | PNAC-II | | 1888.37 |

It can be seen from the data in Tables 7-9, the absolute bioavailability of the single oral SNAC group is 0.88%, while the absolute bioavailability of the single oral PNAC-II group is 1.28%, and the absolute bioavailability of the single oral PNAC-I group is 1.11%; the bioavailability of the two PNAC groups is significantly higher than that of the SNAC group.

Compared with the single oral SNAC group, the absolute bioavailability of the single oral PNAC-II group is increased by 45.5%, and the absolute bioavailability of the single oral PNAC-I group is increased by 26.1%.

Experimental Example 3: Effects of Different Contents and Different Crystal Forms of PNAC on the Bioavailability of GLP-1 Peptide in Beagle Dogs For the preparation method of GLP-1 peptide M4 (M4 for short), please refer to PCT application WO2019201328.

For the preparation method of the combined oral tablet, refer to the preparation method in Example 1 of PCT WO2012080471. The delivery agents (SNAC, PNAC-I, and PNAC-II) were respectively combined with M4. The combined oral tablet prepared by combining SNAC and M4 was SNAC+M4. The combined oral tablet prepared by combining PNAC-I and M4 was PNAC-I+M4. The combined oral tablet prepared by combining PNAC-II and M4 was PNAC-II+M4.

In the combined oral tablet, the ingredients per tablet: M4 content is 10 mg, and the delivery agent content is 300 mg and 450 mg, respectively.

Prescription for intravenous injection of M4: M4 is dissolved in 8 mM phosphate buffer (pH 7.2) to give a final M4 concentration of 1 mg/mL.

Twenty-eight male beagle dogs with body weights of 9-15 kg were selected, and divided into 7 groups with 4 dogs in each group, so as to compare the effects of different crystal forms of PNAC on the bioavailability of M4 in beagle dogs. The grouping information is shown in Table 10 below.

Figure 19:
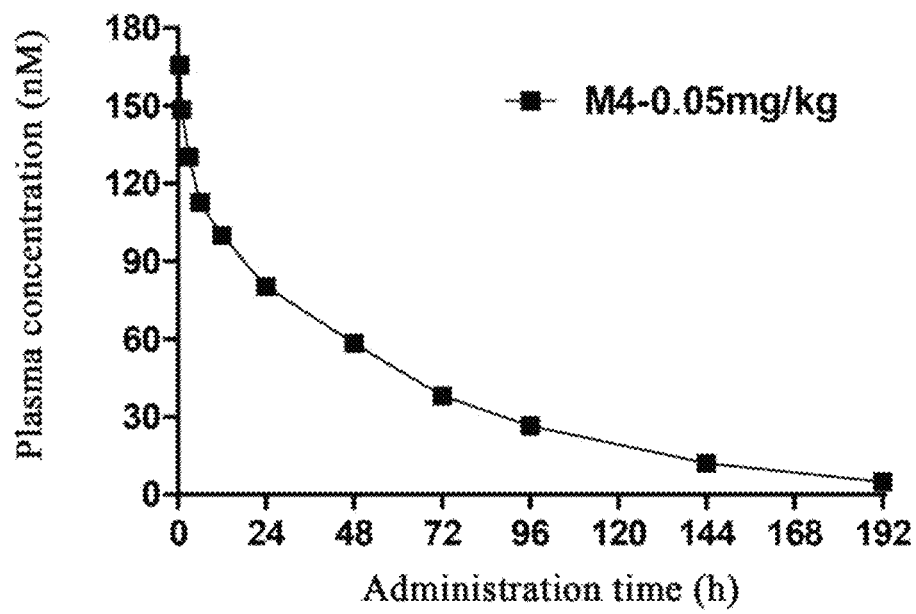
FIG. 19 is a trend plot of plasma concentration vs. administration time in the intravenous administration group.
Figure 20:
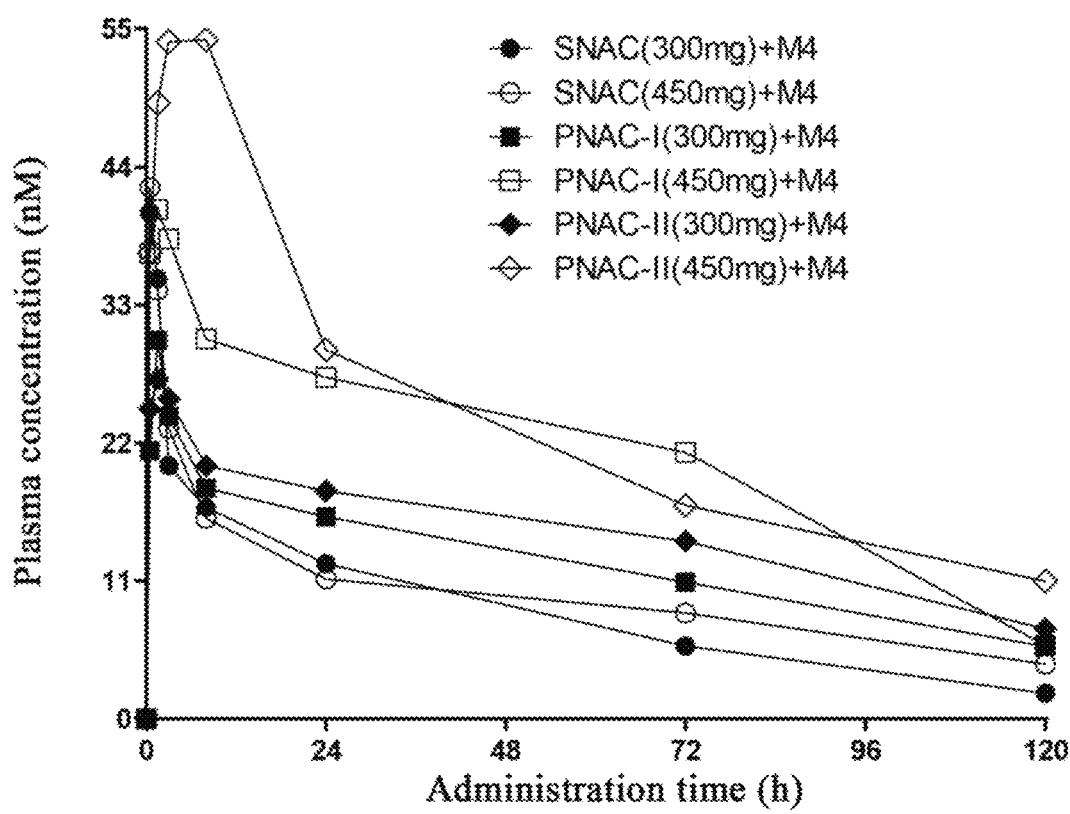
FIG. 20 is a trend plot of plasma concentration vs. administration time in each of the oral administration groups.

The beagle dogs in the oral administration groups were fasted with free access to water in the previous night. On the same day, the tablet was taken with 0 ml of water (quantitative), and 4 h later food intake was resumed for the dogs. Then the plasma concentrations at different time points were measured according to the plasma sampling scheme in Table 11, and the exposure $AUC_{last}$ in animals was calculated. The specific results are shown in Tables 12-14 and FIGS. 19-20.

TABLE 10

Grouping information

| Groups | Route of administration | Dosage of administration | Animal number |
| --- | --- | --- | --- |
| M4 | i.v. | 0.05 mg/kg | 4 |
| SNAC (300 mg) + M4 | p.o. | 300 + 10 mg/tablet | 4 |
| SNAC (450 mg) + M4 | p.o. | 450 + 10 mg/tablet | 4 |
| PNAC-I (300 mg) + M4 | p.o. | 300 + 10 mg/tablet | 4 |
| PNAC-I (450 mg) + M4 | p.o. | 450 + 10 mg/tablet | 4 |
| PNAC-II (300 mg) + M4 | p.o. | 300 + 10 mg/tablet | 4 |
| PNAC-II (450 mg) + M4 | p.o. | 450 + 10 mg/tablet | 4 |

TABLE 11

The plasma sampling schemes

| Groups | Time points of plasma sampling |
| --- | --- |
| M4 intravenous injection group | predose, 0.5, 1, 3, 6, 12, 24, 48, 72, 96, 144, and 192 h after the dosing |
| Oral administration group | predose, 0.5, 1.5, 3, 8, 24, 72, and 120 h after the dosing |

Note:
At least 500 μl plasma, at each time point.

TABLE 12

Summary of plasma concentrations at different time points in the intravenous administration group

| | Plasma concentration (nM)-Administrationtime (h) | | | | | | | | | | |
| --- | --- | --- | --- | --- | --- | --- | --- | --- | --- | --- | --- |
| Group | 0 h | 0.5 h | 1 h | 3 h | 6 h | 12 h | 24 h | 48 h | 72 h | 96 h | 144 h | 192 h |
| M4 | 0 | 165.48 | 148.39 | 130.11 | 112.59 | 99.76 | 80.12 | 58.29 | 38.03 | 26.48 | 12.10 | 4.89 |

TABLE 13

Summary of the plasma concentrations at different time points in each oral administration group

| | Plasma concentration (nM)-Administration time (h) | | | | | | | |
| --- | --- | --- | --- | --- | --- | --- | --- | --- |
| Groups | 0 h | 0.5 h | 1.5 h | 3 h | 8 h | 24 h | 72 h | 120 h |
| SNAC 300 mg | 0.00 | 40.37 | 35.12 | 20.19 | 16.86 | 12.37 | 5.81 | 2.03 |
| SNAC 450 mg | 0.00 | 42.37 | 34.19 | 23.15 | 15.98 | 11.16 | 8.45 | 4.38 |
| PNAC-I 300 mg | 0.00 | 21.38 | 30.20 | 24.15 | 18.39 | 16.12 | 10.89 | 5.76 |
| PNAC-I 450 mg | 0.00 | 37.14 | 40.64 | 38.27 | 30.30 | 27.24 | 21.27 | 5.87 |
| PNAC-II 300 mg | 0.00 | 24.76 | 27.09 | 25.51 | 20.20 | 18.16 | 14.18 | 7.17 |
| PNAC-II 450 mg | 0.00 | 37.19 | 49.11 | 53.94 | 54.10 | 29.44 | 17.02 | 10.98 |

TABLE 14

Summary of drug exposure ($AUC_{last}$) comparison in animals of each group

| Groups | Route of administration | $AUC_{last}$ (nM*h) |
| --- | --- | --- |
| M4-0.05 mg/kg | Intravenous injection | 7403.28 |
| SNAC (300 mg) + M4 | Oral administration | 1040.27 |
| SNAC (450 mg) + M4 | | 1185.38 |
| PNAC-I (300 mg) + M4 | | 1502.17 |
| PNAC-I (450 mg) + M4 | | 2554.68 |
| PNAC-II (300 mg) + M4 | | 1781.28 |
| PNAC-II (450 mg) + M4 | | 2855.20 |

It can be seen from Table 14 that, the absolute bioavailability of the single oral SNAC (300 mg) group is 0.70%, the absolute bioavailability of the single oral SNAC (450 mg) group is 0.80%; while the absolute bioavailability of the single oral PNAC-II group (300 mg) group is 1.20%, and the absolute bioavailability of the single oral PNAC-II group (450 mg) group is 1.92%; the absolute bioavailability of the single oral PNAC-I (300 mg) group is 1.01%, and the absolute bioavailability of the single oral PNAC-I (450 mg) group is 1.72%. Each of the absolute bioavailability of the single oral PNAC group is significantly higher than that of SNAC, meanwhile the absolute bioavailability of administration group increases significantly with the increase of PNAC content.

Compared with the single oral SNAC (300 mg) group, the absolute bioavailability of the single oral PNAC-II (300 mg) group is increased by 71%, and the absolute bioavailability of the single oral PNAC-I (300 mg) group is increased by 44%. Compared with the single oral SNAC (450 mg) group, the absolute bioavailability of the single oral PNAC-II (450 mg) group is increased by 140%, and the absolute bioavailability of the single oral PNAC-I (450 mg) group is increased by 115%.

From the perspective of a single drug, comparing the absolute bioavailability of the single oral SNAC (300 mg) group with that of the single oral SNAC (450 mg) group it is only increased by 14%, and the bioavailability of the two groups are not much different. It indicates that the content of SNAC in a drug has little effect on absolute bioavailability. However, comparing the absolute bioavailability of the single oral PNAC-II (300 mg) group with that of the single oral PNAC-II (450 mg) group it is increased by 60%; and comparing the absolute bioavailability of the single oral PNAC-I (300 mg) group with that of the single oral PNAC-I (450 mg) group it is increased by 70%. Combined with the absolute bioavailability of the single oral PNAC-II and PNAC-I (100 mg) groups in Example 2, it may be further verified that the absolute bioavailability of the PNAC according to the present application increases significantly with the increase of its content, and bring an unexpected qualitative improvement.

Experimental Example 4: Experiments on Solid-State Stability of PNAC Crystal Form II The crystal Form II prepared in Example 2 was divided into three groups. The first group was kept at 60° C. for 24 h to obtain a solid sample. The second group was kept under conditions of 40° C. and 75% relative humidity for two weeks to obtain a solid sample. The third group was kept under the conditions of 25° C. and 60% relative humidity for 2 weeks to obtain a solid sample, and then the three groups of solid samples were respectively evaluated for physical and chemical stability by XRPD and HPLC assay.

The HPLC assay refers to taking the crystal Form II obtained in Example 2 as a reference sample, and the purity obtained by the HPLC purity assay was set as 100 area %, and relative purity=HPLC purity/reference sample purity. In the HPLC assay, a C18 reversed-phase chromatographic column with a column length of 150 mm was used, the mobile phase was acetonitrile-water+0.05% trifluoroacetic acid system, the flow rate was 1.2 ml/min, and the sample was detected under the condition of the detector wavelength UV-215 nm. The purity of main peak was calculated by normalization method.

Figure 11:
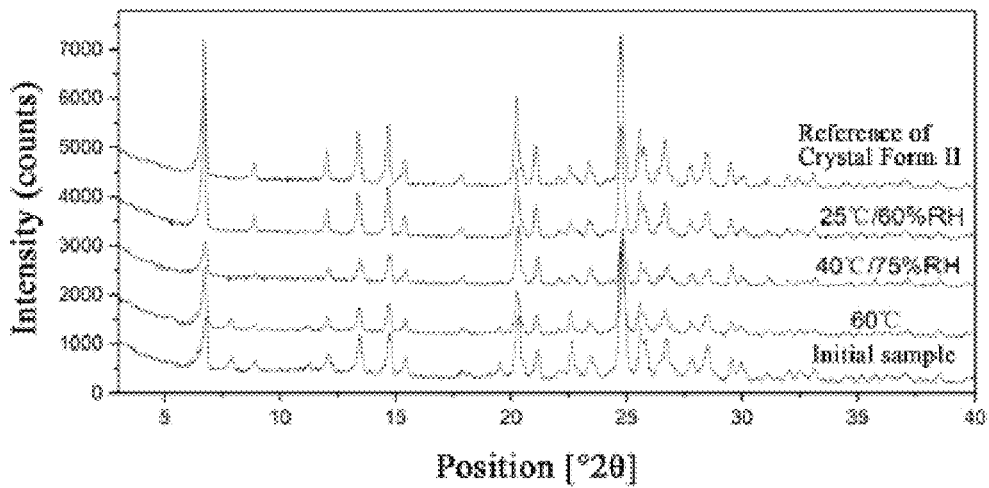
FIG. 11 is an XRPD pattern of crystal Form II in the solid-state stability experiment.

After detection it was found that, the relative purity of the reference sample measured by HPLC was 100% after keeping it in different environments for a set time. The XRPD overlay after the experiment is shown in FIG. 11, which is exactly the same as the characteristic peaks of the reference sample. It can be seen that the crystal form has not changed in the solid-state stability experiment.

Figure 15:
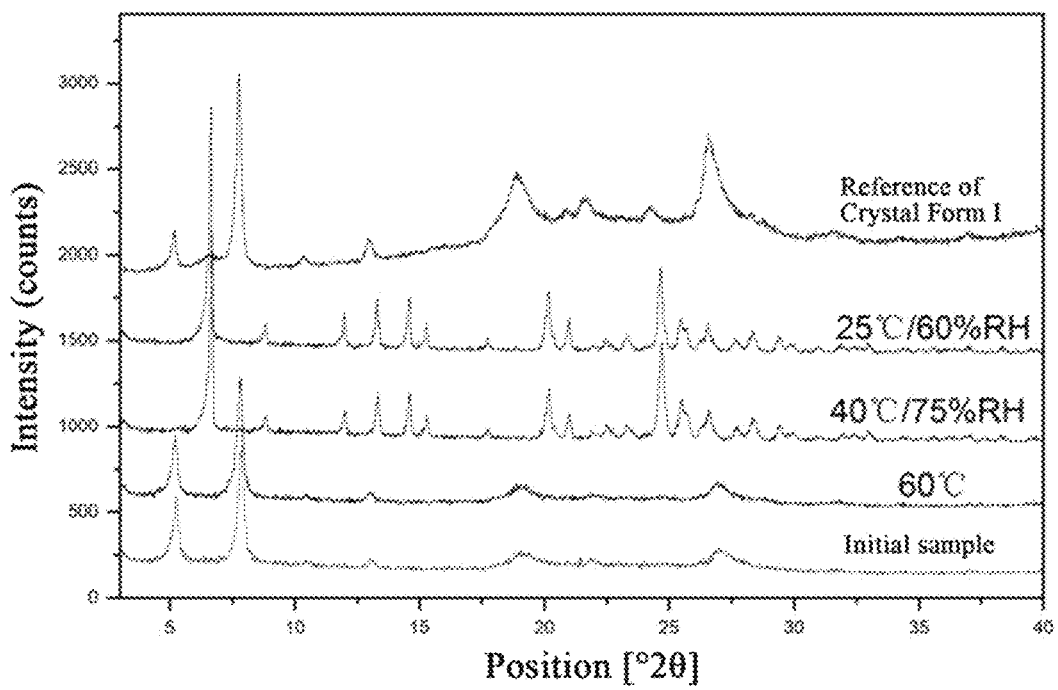
FIG. 15 is an XRPD pattern of crystal Form I in the solid-state stability experiment.

The experiments on solid-state stability of PNAC crystal Form I were carried out by the same method as described above, and the results are shown in FIG. 15.

Experimental Example 5: Experiments on the Stability During Preparation

The crystal Form II obtained in Example 2 was divided into three groups. In the first group, the crystal Form II was manually ground for 10 min to obtain a solid sample. In the second group, the crystal Form II was tableted (pressure of 3 kN) to obtain a solid sample. In the third group, airflow crushing was performed on crystal Form II (injection pressure of 0.4 MPa, pulverization pressure of 0.2 MPa) to obtain a solid sample. Three groups of solid samples were characterized by XRPD to evaluate their physical stability. The specific results are shown in FIGS. 12-14.

Figure 12:
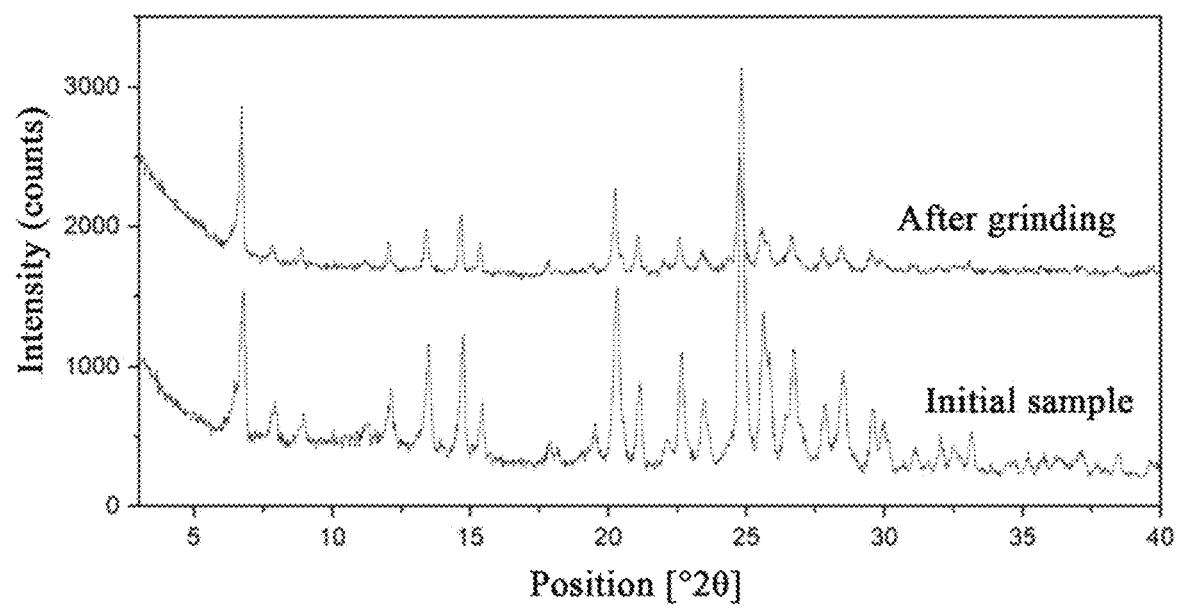
FIG. 12 is the XRPD pattern of crystal Form II before and after the grinding experiment.
Figure 13:
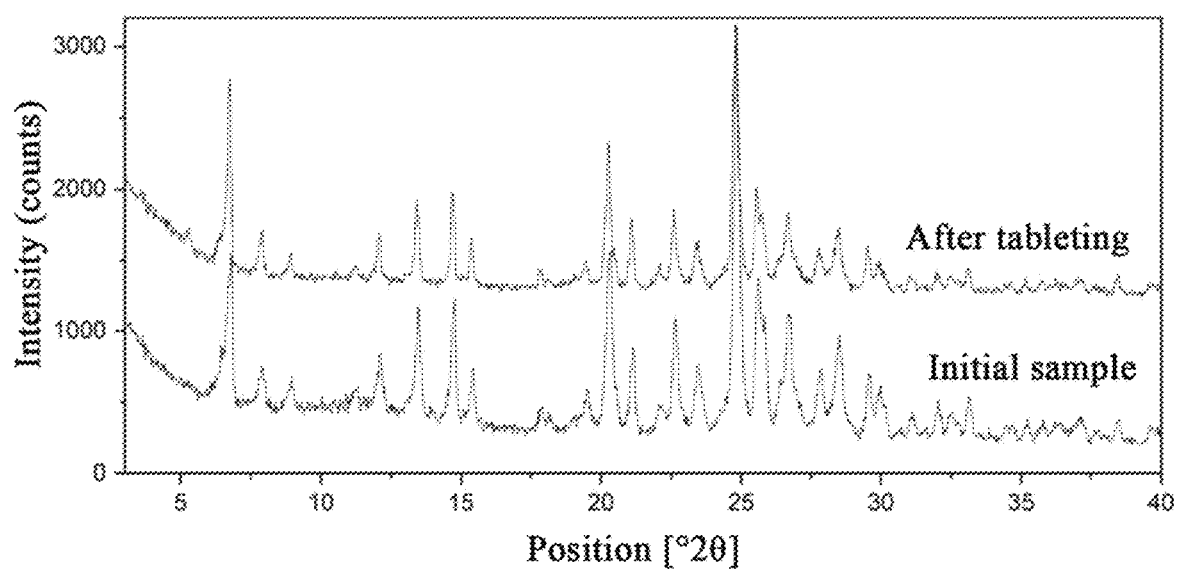
FIG. 13 is the XRPD pattern of crystal Form II before and after the tableting experiment.
Figure 14:
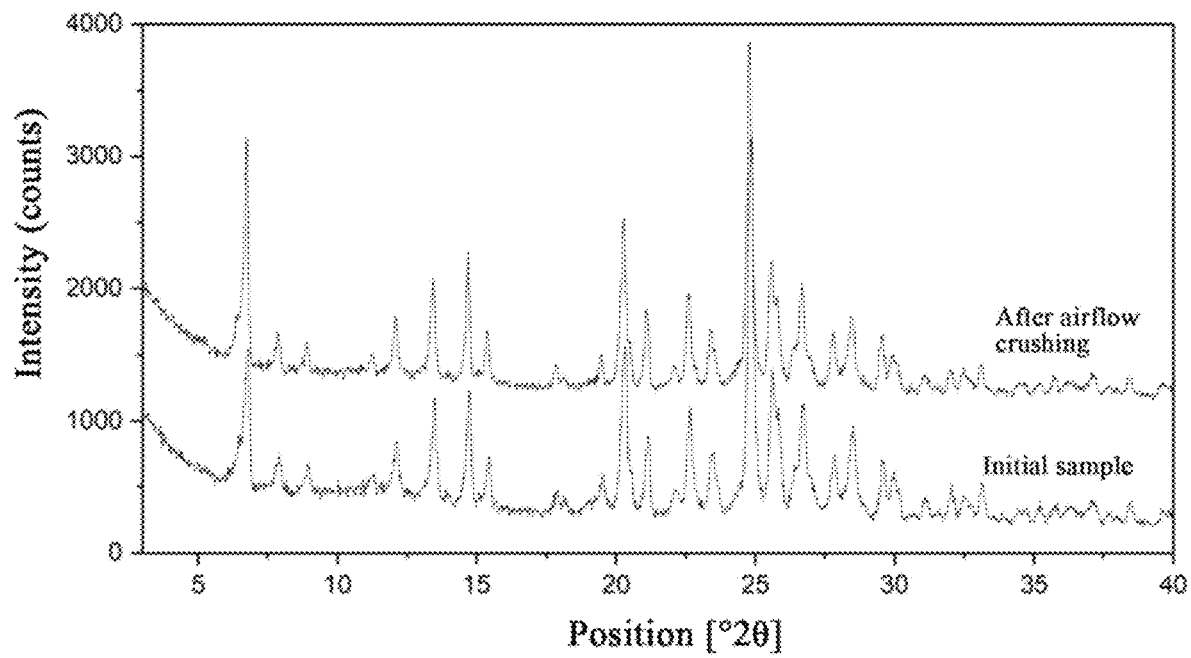
FIG. 14 is the XRPD pattern of crystal Form II before and after the airflow crushing experiment.

It can be seen from FIGS. 12-14 that, after grinding, tableting and airflow crushing of crystal Form II, the crystal form of the samples does not change.

The stability experiments in the preparation process of PNAC crystal Form I, crystal Form II, crystal Form III and crystal Form IV were carried out by using the same method described above, and the results are shown in Table 15.

Figure 16:
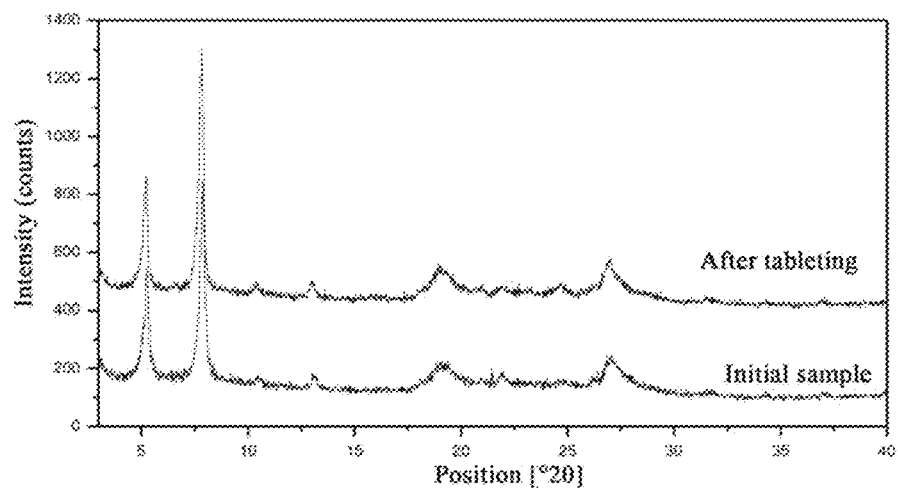
FIG. 16 is the XRPD pattern of crystal Form I before and after the tableting experiment.
Figure 17:
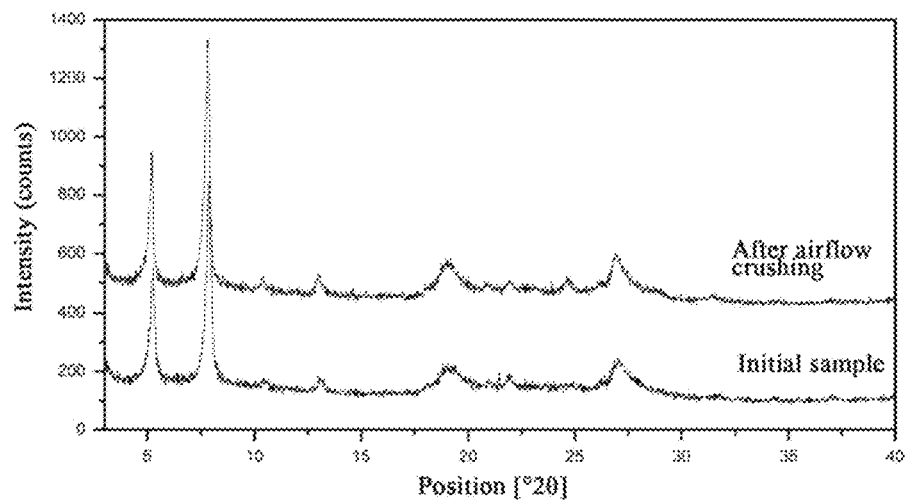
FIG. 17 is the XRPD pattern of crystal Form I before and after the airflow crushing experiment.
Figure 18:
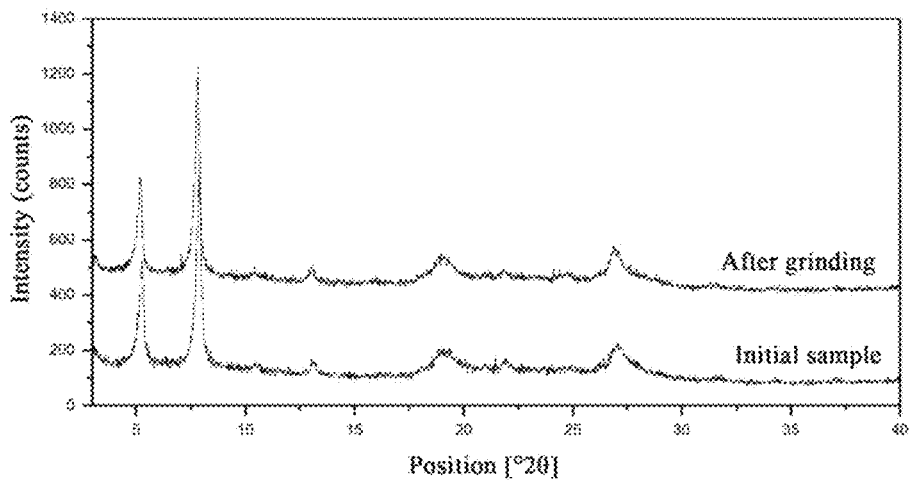
FIG. 18 is the XRPD pattern of crystal Form I before and after the grinding experiment.

The XRPD characterization results of PNAC crystal Form I are shown in FIGS. 16-18. It can be seen from FIGS. 16-18 that, the crystal form of the crystal Form I does not change after grinding, tableting and airflow crushing.

TABLE 15

The results of the experiments on stability of different crystal forms of PNAC

| | Initial crystal form(s) | | | |
|---|---|---|---|---|
| Treatment conditions | crystal Form I | crystal Form II | crystal Form III | crystal Form IV |
| 60° C., 24 h | crystal Form I | crystal Form II | crystal Form I | crystal Form I |
| 25° C./60% RH, 2 W | crystal Form II | crystal Form II | crystal Form II | crystal Form II |
| 25° C./75% RH, 2 W | crystal Form II | crystal Form II | crystal Form II | crystal Form II |
| Manual grinding | crystal Form I | crystal Form II | Mixture of crystal Form II and Form III | crystal Form IV |
| Tableting | crystal Form I | crystal Form II | Mixture of crystal Form II and Form III | crystal Form IV |
| Airflow crushing | crystal Form I | crystal Form II | Mixture of crystal Form II and Form III | crystal Form IV |

From the results in the above table, it can be seen that the PNAC crystal Form I and crystal Form II are very stable, and the crystal Form I will only transform into other crystal form when it is kept in an environment with higher than 60% RH for a long time, while crystal Form II is stable under any conditions in this experiment.

Although the embodiments of the present application are described above, the present application is not limited to the above specific embodiments and application fields, and the above specific embodiments are only illustrative and instructive, rather than restrictive. Under the inspiration of this specification and without departing from the protection scope of claims of this application, the ordinary skilled person in the art can also make many modifications, which all belong to the protection scope of this application.

The invention claimed is:

1. A crystal polymorph of potassium N-[8-(2-hydroxybenzoyl) amino] octanoate, wherein the crystal polymorph of potassium N-[8-(2-hydroxybenzoyl) amino] octanoate is crystal Form I, and the crystal Form I has at least an X-ray powder diffraction pattern with characteristic peaks represented by 2θ° of 7.83±0.2, 26.64±0.2, and 18.89±0.2.

2. The crystal polymorph of potassium N-[8-(2-hydroxybenzoyl) amino] octanoate according to claim 1, wherein the crystal Form I further has at least an X-ray powder diffraction pattern with characteristic peaks represented by 2θ° of 5.24±0.2 or 21.59±0.2.

3. The crystal polymorph of potassium N-[8-(2-hydroxybenzoyl) amino] octanoate according to claim 2, wherein the crystal Form I further has at least an X-ray powder diffraction pattern with characteristic peaks represented by 2θ° of 13.02±0.2 or 24.29±0.2.

4. The crystal polymorph of potassium N-[8-(2-hydroxybenzoyl) amino] octanoate according to claim 3, wherein the crystal Form I further has at least an X-ray powder diffraction pattern with characteristic peaks represented by 2θ° of any one of 6.61±0.2, 10.43±0.2, 31.63±0.2, and 37.00±0.2.

5. The crystal polymorph of potassium N-[8-(2-hydroxybenzoyl) amino] octanoate according to claim 1, wherein the X-ray powder diffraction pattern of the crystal Form I is shown as FIG. 1.

6. The crystal polymorph of potassium N-[8-(2-hydroxybenzoyl) amino] octanoate according to claim 1, wherein the melting point of the crystal Form I is 163.1° C.

7. The crystal polymorph of potassium N-[8-(2-hydroxybenzoyl) amino] octanoate according to claim 1, wherein the adsorption water removal temperature of the crystal Form I is 83.6° C.

8. The crystal polymorph of potassium N-[8-(2-hydroxybenzoyl) amino] octanoate according to claim 1, wherein the crystal Form I loses 3.0% of weight at 140° C.

9. A method of preparing a crystal Form I of potassium N-[8-(2-hydroxybenzoyl) amino] octanoate, wherein the method comprises the steps of:
adding an organic solvent into a reaction vessel and stirring, then adding N-[8-(2-hydroxybenzoyl) amino] octanoic acid and stirring evenly, adding potassium hydroxide solution dropwise, after the dropwise addition, concentrating to obtain the crude product;
adding an organic solvent to the crude product to obtain a filter cake after beating and suction filtration, rinsing the filter cake and placing it in a drying oven for drying to obtain the crystal polymorph of potassium N-[8-(2-hydroxybenzoyl) amino] octanoate.

10. The method according to claim 9, wherein the filter cake is rinsed and then put into a drying oven for drying to obtain crystal Form I of potassium N-[8-(2-hydroxybenzoyl) amino] octanoate, wherein the drying temperature is 60-100° C., and the drying time is 30-40 hours.

11. The method according to claim 9, wherein the organic solvent is isopropanol or acetone; and
the concentration of the potassium hydroxide solution is 40-90%.

12. The method according to claim 9, wherein, after adding N-[8-(2-hydroxybenzoyl) amino] octanoic acid, the temperature of the system is raised to 48° C. or above, then potassium hydroxide solution is added dropwise, and, after the dropwise addition, the temperature is maintained to react for 0.5-2 hours;
wherein the N-[8-(2-hydroxybenzoyl) amino] octanoic acid and potassium hydroxide solution is added in a molar ratio of 1:1; and
the beating time after adding the organic solvent to the crude product is 0.5-1.5 hours.

13. A method of preparing a crystal Form I of potassium N-[8-(2-hydroxybenzoyl) amino] octanoate, wherein the crystal forms of potassium N-[8-(2-hydroxybenzoyl) amino] octanoate other than crystal Form I are heated to at least 75° C. to produce crystal Form I;
the crystal forms of potassium N-[8-(2-hydroxybenzoyl) amino] octanoate other than crystal Form I are at least one or more of crystal Form II, crystal Form III and crystal Form IV; and
the crystal Forms of potassium N-[8-(2-hydroxybenzoyl) amino] octanoate, other than crystal Form I, are heated to 75° C. or above under nitrogen protection to produce crystal Form I of potassium N-[8-(2-hydroxybenzoyl) amino] octanoate.

14. The method according to claim 13, wherein the crystal Form II of potassium N-[8-(2-hydroxybenzoyl) amino] octanoate is heated to 140° C. under nitrogen protection to produce crystal Form I of potassium N-[8-(2-hydroxybenzoyl) amino] octanoate.

15. The method according to claim 13, wherein the crystal Form IV of potassium N-[8-(2-hydroxybenzoyl) amino] octanoate is heated to 110° C. under nitrogen protection to produce crystal Form I of potassium N-[8-(2-hydroxybenzoyl) amino] octanoate.

16. A method of preparing crystal Form I of potassium N-[8-(2-hydroxybenzoyl) amino] octanoate, wherein the crystal forms of potassium N-[8-(2-hydroxybenzoyl) amino] octanoate, other than crystal Form I, are lyophilized to produce crystal Form I;
the crystal forms of potassium N-[8-(2-hydroxybenzoyl) amino] octanoate, other than crystal Form I, are at least one or more of crystal Form II, crystal Form III and crystal Form IV; and
the crystal Form I is crystal Form I of potassium N-[8-(2-hydroxybenzoyl) amino] octanoate according to claim 1.

17. A pharmaceutical composition comprising a crystal polymorph of potassium N-[8-(2-hydroxybenzoyl) amino] octanoate;
wherein the crystal polymorph of potassium N-[8-(2-hydroxybenzoyl) amino] octanoate is crystal Form I.

18. The pharmaceutical composition according to claim 17, further comprising a preventive and/or therapeutic drug;
wherein, in the pharmaceutical composition, the weight ratio of the crystal polymorph of potassium N-[8-(2-hydroxybenzoyl) amino] octanoate to the preventive and/or therapeutic drug is (20-60): 1.

19. The pharmaceutical composition according to claim 18, wherein the preventive and/or therapeutic drug is one or more of glucagon-like peptide-1, insulin, PYY, human amylin, heparin, human growth hormone, interferon, monoclonal antibody, protease inhibitor, and thrombopoietin.

* * * * *